(12) United States Patent
Hacking et al.

(10) Patent No.: US 9,456,902 B2
(45) Date of Patent: Oct. 4, 2016

(54) ORTHOPAEDIC IMPLANTS

(71) Applicant: THE ROYAL INSTITUTION FOR THE ADVANCEMENT OF LEARNING / MCGILL UNIVERSITY, Montreal (CA)

(72) Inventors: Adam S. Hacking, Somerville, MA (US); Edward J. Harvey, Montreal (CA); Corey Richards, Alderley (AU)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 0 days.

(21) Appl. No.: 14/097,654

(22) Filed: Dec. 5, 2013

(65) Prior Publication Data

US 2014/0094924 A1  Apr. 3, 2014

Related U.S. Application Data

(62) Division of application No. 12/809,030, filed as application No. PCT/CA2008/002179 on Dec. 17, 2008, now abandoned.

(60) Provisional application No. 61/008,173, filed on Dec. 18, 2007.

(51) Int. Cl.
| | |
|---|---|
| *A61F 2/28* | (2006.01) |
| *A61F 2/30* | (2006.01) |
| *A61B 17/15* | (2006.01) |
| *A61F 2/42* | (2006.01) |
| *A61B 6/00* | (2006.01) |

(52) U.S. Cl.
CPC .......... *A61F 2/30942* (2013.01); *A61B 17/15* (2013.01); *A61F 2/28* (2013.01); *A61F 2/4261* (2013.01); *A61B 6/505* (2013.01); *A61B 2034/102* (2016.02); *A61F 2002/2871* (2013.01); *A61F 2002/30069* (2013.01); *A61F 2002/30945* (2013.01); *A61F 2002/30948* (2013.01); *A61F 2002/30957* (2013.01); *A61F 2002/4289* (2013.01); *A61F 2240/004* (2013.01); *A61F 2310/00011* (2013.01); *A61F 2310/00179* (2013.01); *Y10T 29/49* (2015.01)

(58) Field of Classification Search
CPC ................ A61F 2/30942; A61F 2002/30962; A61F 2002/30948; A61F 2/4261; A61F 2/28; A61F 2310/00179; A61F 2240/004; A61F 2002/4289; A61F 2002/2871; A61F 2310/00011; A61B 17/15; A61B 2034/102; A61B 6/505; Y10T 29/49
See application file for complete search history.

(56) References Cited

U.S. PATENT DOCUMENTS 4,198,712 A * 4/1980 Swanson ................ 623/21.14
4,436,684 A    3/1984 White
(Continued)

FOREIGN PATENT DOCUMENTS

CN    101259046    9/2008

*Primary Examiner* — Galen Hauth
(74) *Attorney, Agent, or Firm* — Norton Rose Fulbright Canada LLP

(57) ABSTRACT

A method for making an orthopaedic implant, the method comprising: characterizing at least a portion of a bone corresponding to the bone to be replaced, said corresponding bone being on the contralateral side of the patient; providing a model of the orthopaedic implant based on a mirror image of the contralateral bone; and forming the orthopaedic implant based on the model.

16 Claims, 26 Drawing Sheets

(56) References Cited

U.S. PATENT DOCUMENTS

| | | | |
|---|---|---|---|
| 4,936,860 A | 6/1990 | Swanson | |
| 5,702,468 A * | 12/1997 | Goldberg | A61F 2/4225 623/21.12 |
| 5,741,215 A * | 4/1998 | D'Urso | 600/407 |
| 6,059,832 A | 5/2000 | Menon | |
| 6,112,109 A | 8/2000 | D'Urso | |
| 6,126,690 A * | 10/2000 | Ateshian | A61F 2/4241 623/22.4 |
| 7,113,841 B2 * | 9/2006 | Abe et al. | 700/118 |
| 2003/0109784 A1 | 6/2003 | Loh et al. | |
| 2004/0133276 A1 * | 7/2004 | Lang | A61F 2/30756 623/14.12 |
| 2007/0173815 A1 | 7/2007 | Murase | |

* cited by examiner

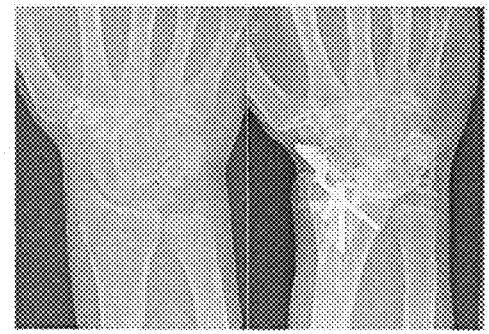
FIG. 26A  FIG. 26B
 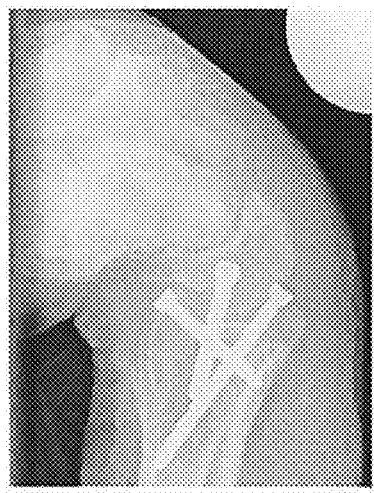
FIG. 27A  FIG. 27B
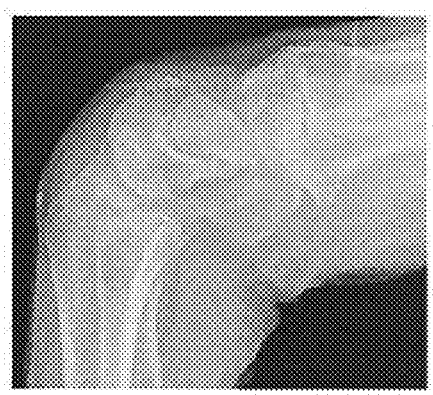 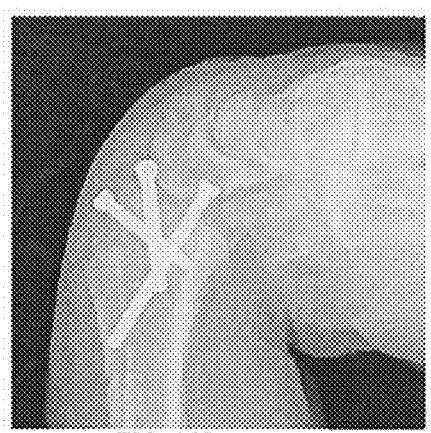
FIG. 28A  FIG. 28B

ORTHOPAEDIC IMPLANTS

CROSS REFERENCE TO RELATED APPLICATIONS

This is a divisional of U.S. patent application Ser. No. 12/809,030 filed Sep. 3, 2010, which is a U.S. National Phase entry of International Patent Application No. PCT/CA2008/002179 filed Dec. 17, 2008, which claims the benefit of U.S. Provisional Patent Application No. 61/008,173 filed Dec. 18, 2007. Each of these applications are incorporated herein in their entirety.

FIELD OF THE INVENTION

The invention relates generally to orthopaedic implants, methods of making the orthopaedic implants, methods of implanting the orthopaedic implants, devices for implanting the orthopaedic implants and devices for assisting cutting bone.

BACKGROUND OF THE INVENTION

Damaged or diseased bones and joints in human and animal patients give rise to pain and decreased joint mobility. It is known to totally or partially replace these bones and joints with artificial implants to alleviate the painful symptoms and restore some degree of mobility.

The replacement of bones in the wrist has had limited success because of the complexity and multitude of bones, tendons and ligaments in the wrist. As can be seen in FIG. 1, there is a first row of wrist bones, known as a first carpal row or proximal carpal row, adjacent a radius bone and an ulnar bone. The proximal carpal row includes a scaphoid bone, a lunate bone, a triquetrum bone and a pisiform bone. A second row of bones, known as a distal carpal row, includes a trapezium bone, a trapezoid bone, a capitate bone and a hamate bone. The scaphoid bone is surrounded by the trapezium, trapezoid, capitate and lunate bones and articulates at the proximal side with a radius bone of the arm, at the distal side with the trapezium and trapezoid of the proximal carpal row, and medially about the lunate and capitate bones. The distal end of the radius bone has a scaphoid fossa, which faces the scaphoid, and a lunate fossa which faces the lunate bone. A ridge separates the scaphoid and the lunate fossas.

The ligaments of the wrist are illustrated in FIGS. 2A and 2B for two different patients demonstrating the complexity of the wrist anatomy and the variability of the wrist anatomy between different patients. These ligaments include the radial collateral ligament (RC), the radioscaphocapitate ligament (RSC), the radiolunate ligament (RL), the ulnolunate ligament (UL), the ulnocarpal meniscus homologue (M), the lunotriquetral ligament (LT), the deltoid ligament (V), dorsal scapholunate ligament (SL), dorsal interior circular muscle unit (DIC), ulnar collateral (UC), radioscapholunate ligament (RSL), trapezoid-trapezium (TT), trapezoid-capitate (TC), capitohamate (CH), radioscaphoid (RS), radiotriquetral (RT). The Volar FCR tendon and the volar capsule also form part of the wrist anatomy but are not shown in FIGS. 2A and 2B.

Replacement of some of the bones of the wrist may be required to treat bone fractures, or diseases such as arthritis which affects the radius joint of the wrist. Arthritis more commonly affects elderly patients and results in painful joints, and may be so severe that the pain cannot be managed with pain medication and the arthritic hand cannot be used to lift weight. Wrist bone fractures, seen typically in younger patients, occur most often in the scaphoid bone. Damage or degeneration to the scaphoid bone can also occur through conditions other than fracture. The scaphoid bone is particularly difficult to heal since blood supply to the scaphoid bone is provided only by vessels on the distal side. If not treated properly or detected early, a scaphoid bone fracture can lead to bone necrosis.

Total or partial wrist replacements are known to treat arthritis in the wrist and involve the replacement of several bones in the wrist using a total wrist replacement prosthesis formed from biomaterials such as metal, polypropylene or silicone elastomers. In one known total wrist replacement system, the bones of the first carpal row are removed and replaced by an implant which fuses together the bones above the first carpal row and which has an articulating surface for articulating against the radius or a surface implant replacing the surface of the radius. With this type of replacement, the pain may be somewhat alleviated although patients cannot retain full functional flexibility and use of their hand. These types of replacements can also loosen through trauma or injury sustained through a fall, for example, or through wear, and therefore require replacement. Partial wrist replacements are a less severe type of replacement. A known partial wrist replacement technique involves the replacement of the scaphoid and lunate bones of the proximal carpal row with an implant which functions as a spacer to maintain the relationship of adjacent carpal bones after excision of the scaphate or lunar bones.

The known early treatment for scaphoid bone fracture is anatomic reduction with internal fixation. Known fixation devices include Herbert's screw, the Acutrack Acumed™ screw, as well as other screw types. Typically, the fractured scaphoid bone and/or its fragments are removed and some of the remaining bones are fixed to one another using one or more screws. Clearly, this can restrict the range of movement of the patient's wrist and is not ideal. Late treatment involves the treatment of resultant arthritis with a partial or total wrist replacement. Ligament injury between the scaphoid and lunate is often missed and the most common treatment is partial or total wrist replacement.

The bones of the human or animal foot can suffer from similar damage or diseases as the wrist. As for the wrist, there is a lack of effective treatment for damaged or diseased foot bones and ligaments.

Therefore, it is desired to overcome or reduce at least some of the above-described problems.

SUMMARY OF THE INVENTION

The present invention reduces the difficulties and disadvantages of the aforesaid designs and treatments.

From one aspect, there is provided a method for making an orthopaedic implant, the method comprising characterizing at least a portion of a bone corresponding to the bone to be replaced, said corresponding bone being on the contralateral side of the patient; providing a model of the orthopaedic implant based on a mirror image of the contralateral bone; and forming the orthopaedic implant based on the model. The dimensions of the body of the implant can correspond substantially with the contralateral bone of the bone being replaced as it has been found that for some bones of the human or animal body, the contralateral bones are mirror images of one another.

Advantageously, the model is a three-dimensional image, and the characterizing comprises imaging the at least a portion of the bone corresponding to the bone to be replaced using Magnetic Resonance Imaging or Computed Tomography, or the like.

Optionally, the model may be processed before forming the orthopaedic implant. The processing may include modifying a surface feature such as applying a surface topography. The surface topography to be applied can be based on an articulating surface topography of an articulating bone intended to articulate with a surface of the bone to be replaced, the method further comprising characterizing the articulating surface topography of the adjacent bone and applying the characterized surface topography to the model.

The processing may also include adding an attachment element to the model, the attachment element being at least one opening in the orthopaedic implant for attaching the orthopaedic implant to surrounding soft or hard tissue in use. Alternatively, the attachment element, such as at least one opening, may be formed on the orthopaedic implant.

Preferably, the orthopaedic implant is formed from the model by stereolithography. Therefore, the orthopaedic implant can be easily and relatively inexpensively manufactured from suitable biocompatible materials.

In one embodiment, the bone being replaced is the scaphoid bone.

In another embodiment, the method further comprises making a replacement articulating component for articulating against a portion of the orthopaedic implant in use, the method comprising: providing a model of an articulating bone to be replaced; and forming the replacement articulating component from the model.

Advantageously, providing the model of the articulating bone includes imaging the articulating bone or the patient's contralate*ral articulating bone. The model can be a 3D digital model.

The method can further comprise processing the model before forming the replacement articulating component. The processing can include modifying a surface to apply a surface topography by characterizing a surface topography of the articulating bone or the patient's contralateral articulating bone and applying it to the model.

Optionally, at least one attachment element can be formed on the model or on the replacement articulating component. Preferably, the at least one attachment element is an opening formed through the replacement articulating component for receiving a fixation device, such as a nail or a screw.

The model can also be processed to adjust the outer dimensions of the model to minimize the amount of bone being replaced. In this way, trauma to the surrounding is minimized.

From another aspect, there is provided an implant for replacing bone, said implant having a body which is sized and shaped to anatomically replicate the bone being replaced and which is based on a mirror image of a corresponding bone on a contralateral side of a patient. Advantageously, the implant body includes at least one attachment element for attaching the implant to soft or hard tissue at a site of implantation in use. The at least one attachment element can be an opening formed through the implant body.

In one embodiment, the bone being replaced is a scaphoid bone of a wrist, the implant being surgically insertable at an implantation site adjacent trapezium, trapezoid, lunate, capitate and radius bones, the implant body having a capitate articulating surface, a radius articulating surface and a lunate articulating surface. The outer dimensions of the implant are based on outer dimensions of a scaphoid bone on the contralateral side of the patient. The surface topography of the radius articulating surface of the scaphoid implant is based on a surface topography of a corresponding articulating surface of the radius bone or a corresponding articulating surface of a contralateral radius bone.

The implant may further comprise a component for replacing at least a portion of a surface of a bone articulating against the implant in use, the component comprising a component body and a component surface, the component surface corresponding substantially in topography to the portion of the surface of the articulating bone which the component is replacing, to a corresponding contralateral bone, or to an articulating surface of the implant. Preferably, the component body includes at least one component attachment element, such as an opening formed through the component body, for attaching the component to the articulating bone.

In one embodiment, the component is arranged to replace at least a portion of the radius bone which articulates against the radius articulating surface of the implant in use.

From a yet further aspect, there is provided an implant for replacing at least a portion of a radius bone of a patient, the implant comprising a radius implant body and a radius implant surface, the radius implant surface corresponding substantially in topography to the portion of the radius bone which the implant is replacing, or to a corresponding articulating surface in use. Preferably, the radius implant body includes at least one radius implant attachment element, such as an opening formed through the radius body, for attaching the implant to the radius bone.

From yet another aspect, there is provided a method for replacing a scaphoid bone of a patient with an implant as described above, the method comprising: removing the scaphoid bone to be replaced at a site of implantation; placing the implant at the site of implantation; and stabilizing the implant in position. Preferably, the implant comprises at least one opening formed in a body of the implant, the method further comprising stabilizing the implant by securing a ligament, tendon or other soft tissue element at the implantation site through the opening. In one embodiment, the method further comprises attaching a dorsal interior circular muscle unit (DIC) ligament to a flexor carpi radialis (FCR) tendon through a first implant opening, and attaching a scapholunate ligament (SL) to a volar capsule through a second implant opening. The implant can be surgically positioned through relatively simple surgical procedures which minimizes surgery time to the benefit to the patient and to the hospital.

From another aspect, there is provided a device for guiding the excision of a portion of an end of a bone; the device comprising a first face arranged to abut an end of the bone, and a second face arranged to abut a side of the end of the bone, the first face comprising a first slot extending to the second face to define a first cutting edge, and the second face comprising a second slot extending across the second face to intersect the first slot to define a second cutting edge. The device can also include at least one attachment element, such as an opening formed through either the first or the second faces, for securing the device to the bone. In one embodiment, the first face is at substantially 90° to the second face. This is suited for excising the distal end of a radius bone. However, different angles are possible according to the shape of the end of the bone being excised.

There is also provided a method for excising a portion of an end of a bone, the method comprising: placing a device as described above over the end of the bone; securing the device in position on the bone; inserting a cutting device into the first or second slot of the device and guiding the cutting device along an edge of the slot to cut the bone along the first and second slots.

From yet another aspect, there is provided a device for guiding the cutting of slices of bone, the device comprising a first face for abutting an end of a bone, and a second face for abutting a side of the end of the bone, a slot for receiving and guiding a cutting device extending across the second face, the slot being spaced from the first face for cutting a slice of the bone from the end of the bone. The device preferably comprises at least one attachment element for securing the device to the bone. The attachment element can be an opening formed through either the first or the second faces for receiving a fixation device such as a wire, nail or screw. In one embodiment, for slicing bone from a distal end of a radius bone, the first face is at substantially 90° to the second face. However, this angle may vary depending on the application.

There is also provided a method for excising a sliver of a bone from an end of the bone, the method comprising placing a device as described above over the end of the bone; securing the device in position on the bone; and inserting a cutting device into the slot and guiding the cutting device along an edge of the slot to cut the bone along the slot.

According to another aspect, there is provided a device for cutting a sliver of a bone, said device comprising: a body portion having two open ends and a bore extending between the two open ends for receiving a piece of the bone from which the sliver is to be cut, the body portion comprising a slot for receiving and guiding a cutting device for cutting the piece of bone in the bore; an end portion for closing one open end of the bore and for supporting the piece of bone when received in the bore; and a plunger portion receivable in the other open end of the bore for keeping the piece of bone in position whilst the sliver is cut from the piece of bone. Using this device, if too much bone has been excised, a sliver of bone can be cut from a piece of cut bone and re-attached to the cut surface of the bone.

Also provided is a method for cutting a sliver from a piece of bone, said method comprising: inserting the piece of bone in the bore of the body portion of the device as described above whilst the end portion closes one of the ends of the body portion; inserting the plunger portion through the other end of the body portion to secure the bone piece in position; and inserting a cutting edge of a cutting device in the slot and guiding the cutting edge along the slot to cut a sliver of the bone.

From yet another aspect, there is provided a method for replacing at least a portion of a radius bone of a patient with an implant as described above, the method comprising excising the portion of the radius bone to be replaced using a device or a method as described above; placing the implant at the site of implantation; and stabilizing the implant in position. Preferably, the implant is stabilized by at least one fixation element, such as screws or nails received through openings in a body of the implant, to secure the implant to the surrounding radius bone. In one embodiment, the scaphoid bone is removed prior to excising the radius bone portion, and the scaphoid bone is replaced with an implant as described above after the portion of the radius bone has been replaced. This provides more space around the distal end of the radius bone for the excision and surface replacement of the radius bone.

From a yet further aspect, there is provided a method for replacing at least a portion of a radius bone of a patient with an implant as described above, the method comprising excising the portion of the radius bone to be replaced; placing the implant at the site of implantation; and stabilizing the implant in position. Advantageously, the implant is stabilized by fixation elements engaging with the implant to secure the implant to the surrounding radius bone. The fixation elements can be screws or nails received through openings in a body of the implant. In one embodiment, a scaphoid bone is removed prior to excising the radius bone portion. The scaphoid bone can then be replaced with an implant as described above after the portion of the radius bone has been replaced.

Yet further aspects of the invention are the use of an implant as described above for replacing damaged bones such as a scaphoid bone and/or a radius bone of a wrist of a patient, and the use of a device as described above for preparing a radius bone for implantation of a radius implant.

Inventors have found that custom scaphoid arthroplasties based on images of the scaphoid bone of the contralateral wrist (mirror image) using computed tomography or magnetic resonance scans produce an anatomical replica of the bone being replaced. Replacing the scaphoid bone alone eliminates the need for surgery with a Herbert screw or a wrist fusion or replacement. Therefore, the damaged scaphoid bone can be replaced immediately or soon after an accident, rather than at a later date, which would limit the risk of developing arthritis later on. The invention could also apply to other damaged bones in the wrist and foot to avoid performing a total wrist replacement or other treatments to the hand and foot.

The feature of the attachment element on the implant provides a way of stabilizing the implant at the implantation site and attaching the implant to nearby soft or hard tissue. Specifically, sutures or other attachment devices can be used to secure ligaments and tendons to the implant, and in turn secure these to the capsular tissue.

Replacing the scaphoid bone alone is new and opens the possibility of treating younger patients with arthritis. By means of the invention, the treatment of damaged bone such as fractured bone and bone defects will be easier and cheaper to carry out. The implant of the embodiments of the invention has the potential for permitting improved wrist motion with increased stability, mobility and freedom from pain compared to prior art implants. By implanting an anatomical replica of the scaphoid bone of the patient being replaced, arthritis or other diseases or mechanical problems of the wrist are avoided. It is believed that the scaphoid implant does not alter the natural healthy biomechanics of the patient's wrist.

Benefits might be very important for young patients that do not have any option at the moment as well as for elderly patients that could avoid a total wrist arthroplasty. The present invention is in line with a new trend of ambulatory/less invasive surgery. An implant is provided that will fit the patient's anatomy based on the mirror image of the contralateral wrist. The implant also has specific regions to fix ligaments. It is unlike existing replacements which are non-anatomic and involve the removal of healthy bones. The embodiments of the invention are envisaged to have application in various orthopaedic procedures, such as wrist and ankle surgery.

BRIEF DESCRIPTION OF THE DRAWINGS

Further aspects and advantages of the present invention will become better understood with reference to the description in association with the accompanying drawings in which:

FIGS. 26 to 28 are x-rays of (A) a contralateral human wrist, and (B) the corresponding wrist having an implanted orthopaedic implant according to an embodiment of the present invention according to FIGS. 3A to 3F and 7A and 7B, and as described in Example 1.

DETAILED DESCRIPTION OF THE INVENTION

Figure 1:
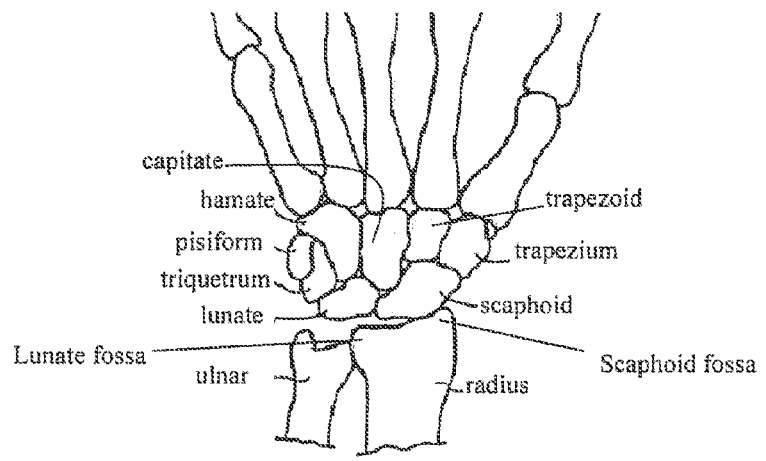
FIG. 1 is a schematic illustration of the principal bones of a wrist of a human right hand when viewed from the palm side of the right hand.
Figure 2A:
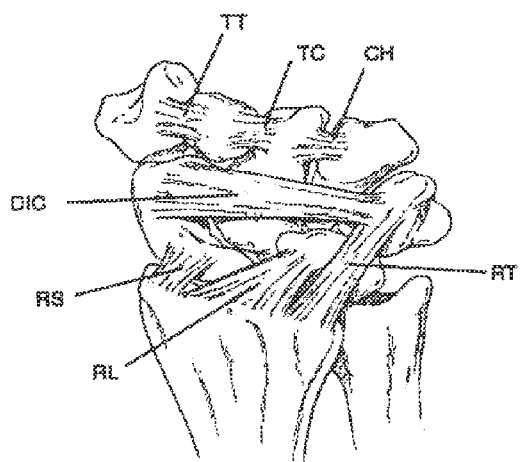
FIGS. 2A and 2B illustrate the tendons and ligaments of the human wrist for two different patients.
Figure 2B:
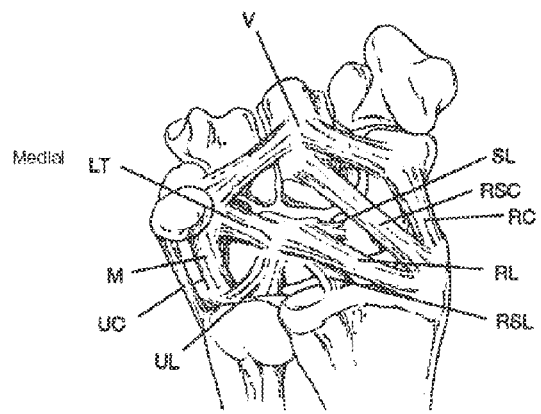
Figure 3A:
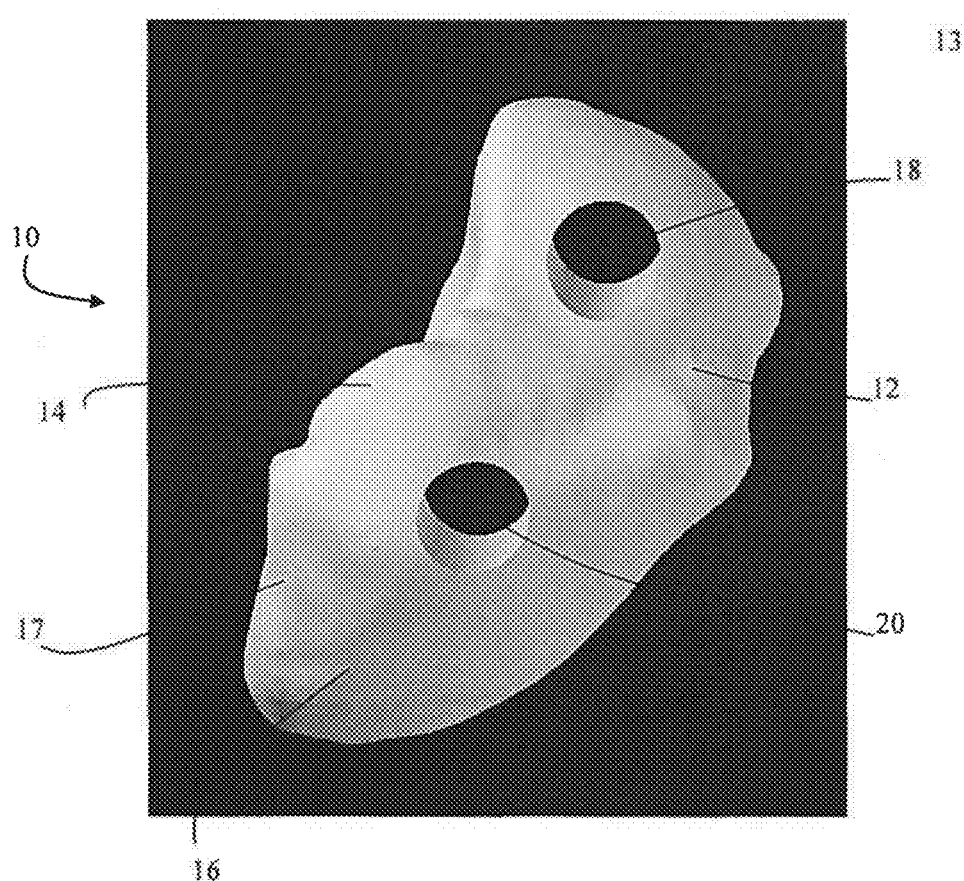
FIGS. 3A to 3F illustrate (A) an anterior view, (B) a distal view, (C) another anterior view, (D) a lateral view, (E) a medial view and (F) a posterior view, of an implant according to one embodiment of the present invention.
Figure 3B:
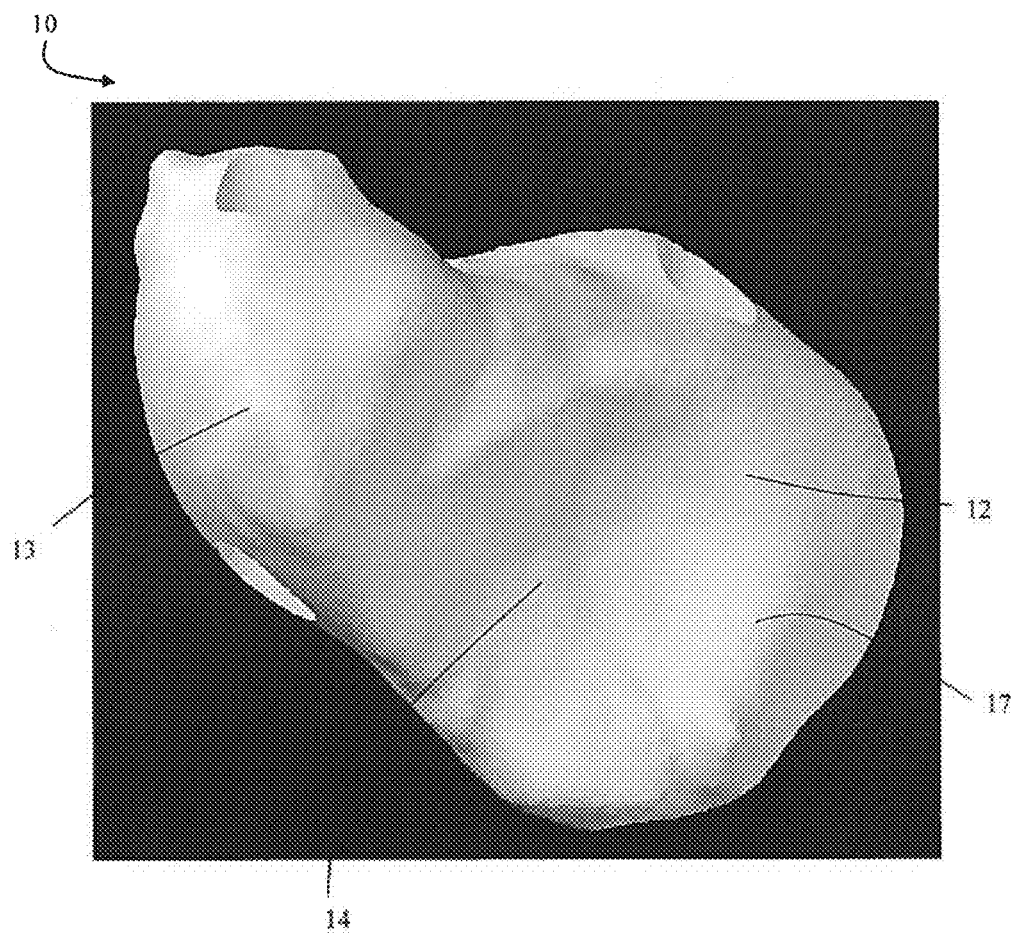
Figure 3C:
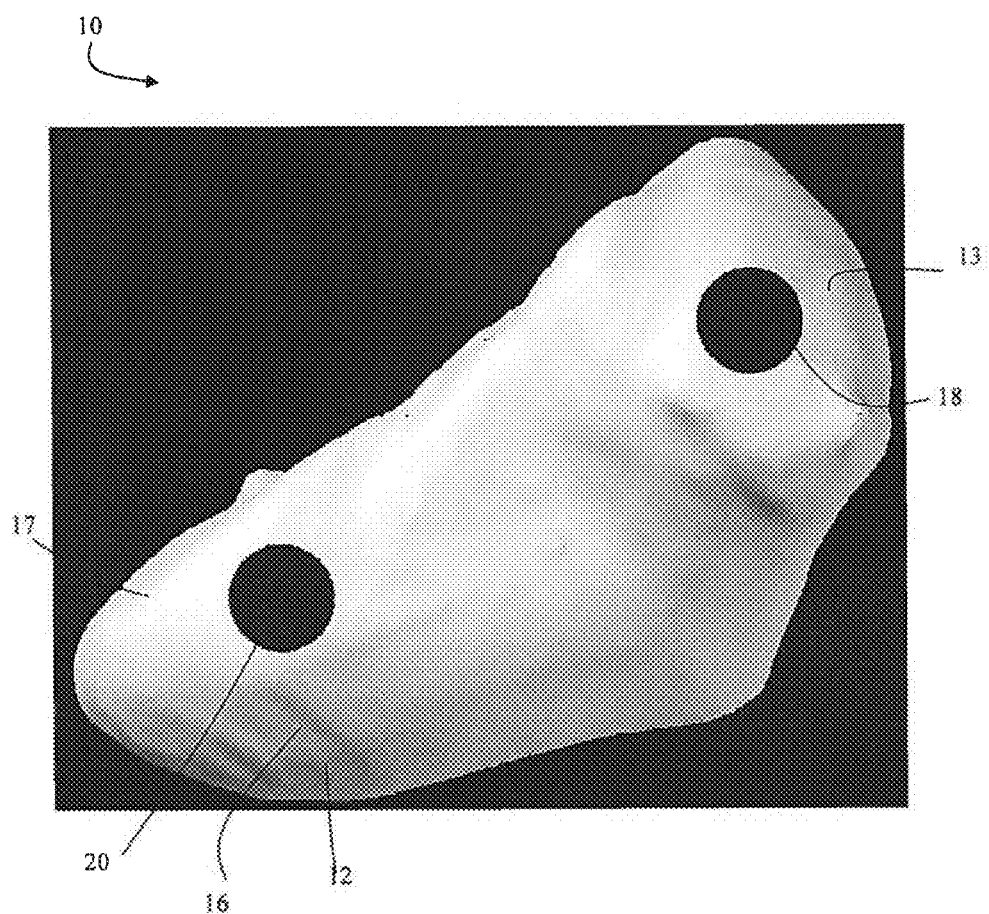
Figure 3D:
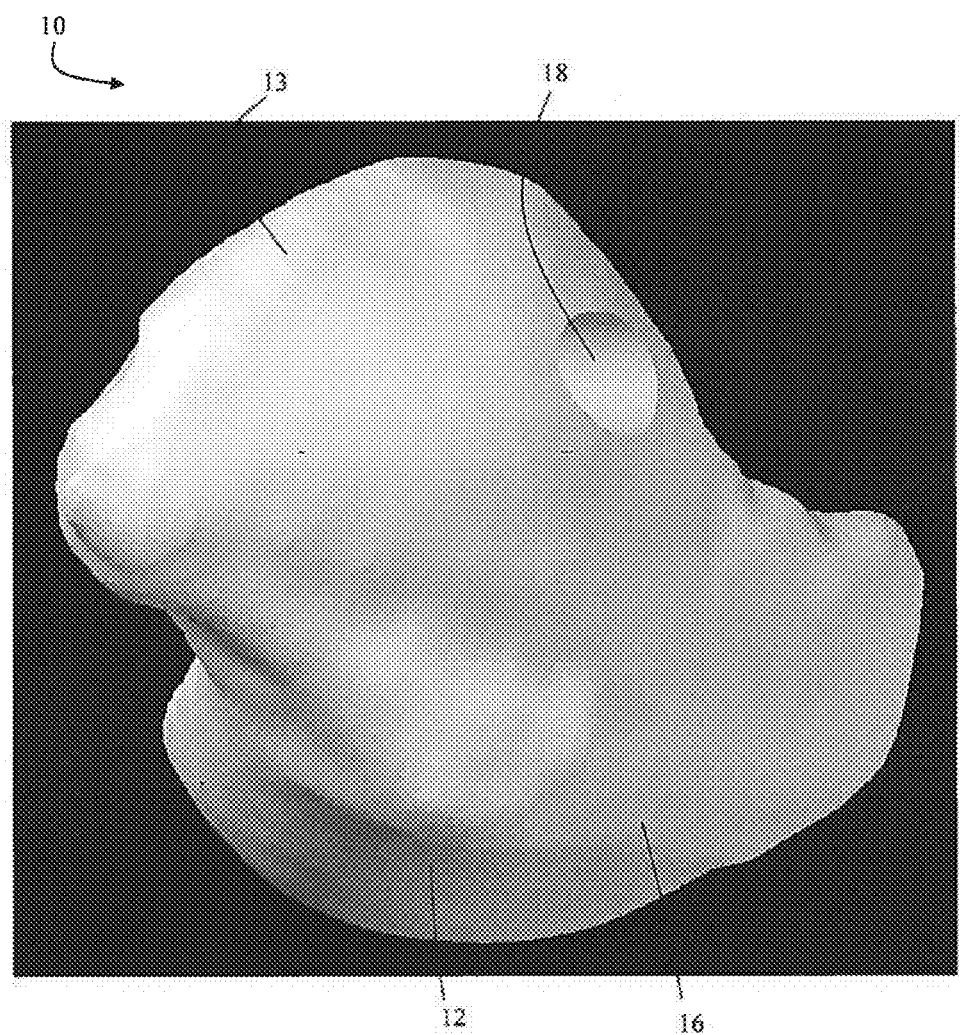
Figure 3E:
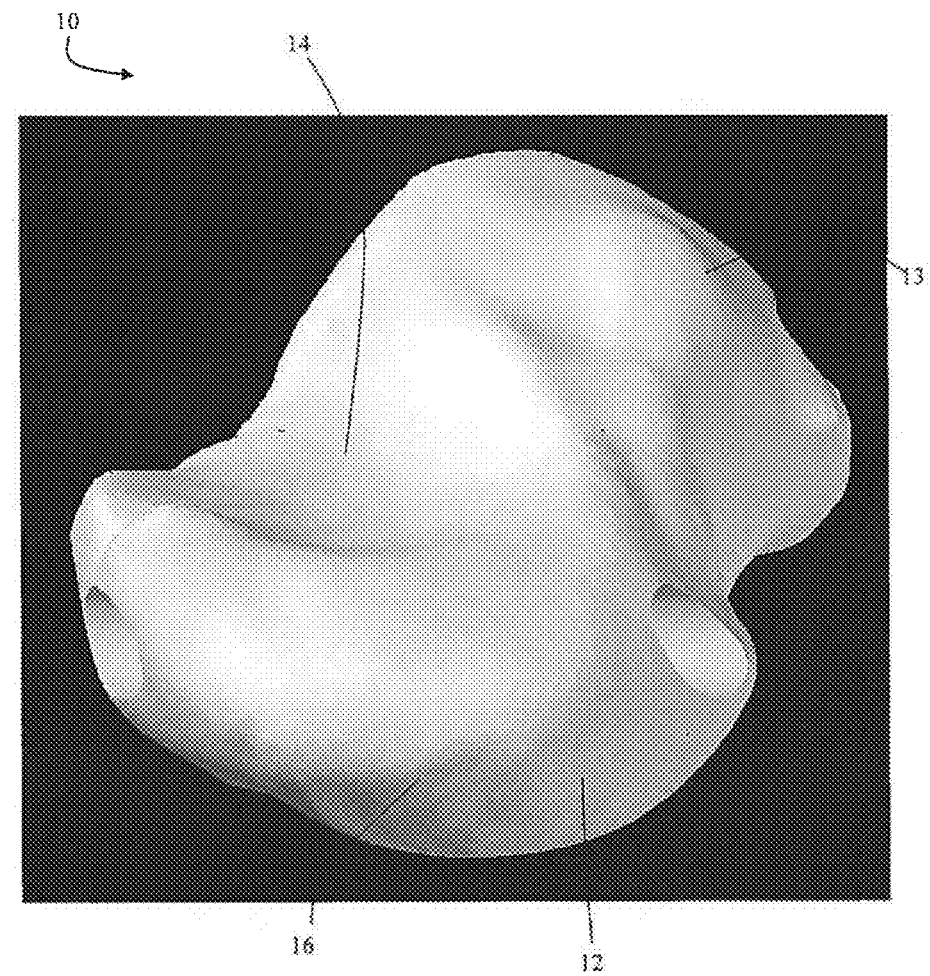
Figure 3F:
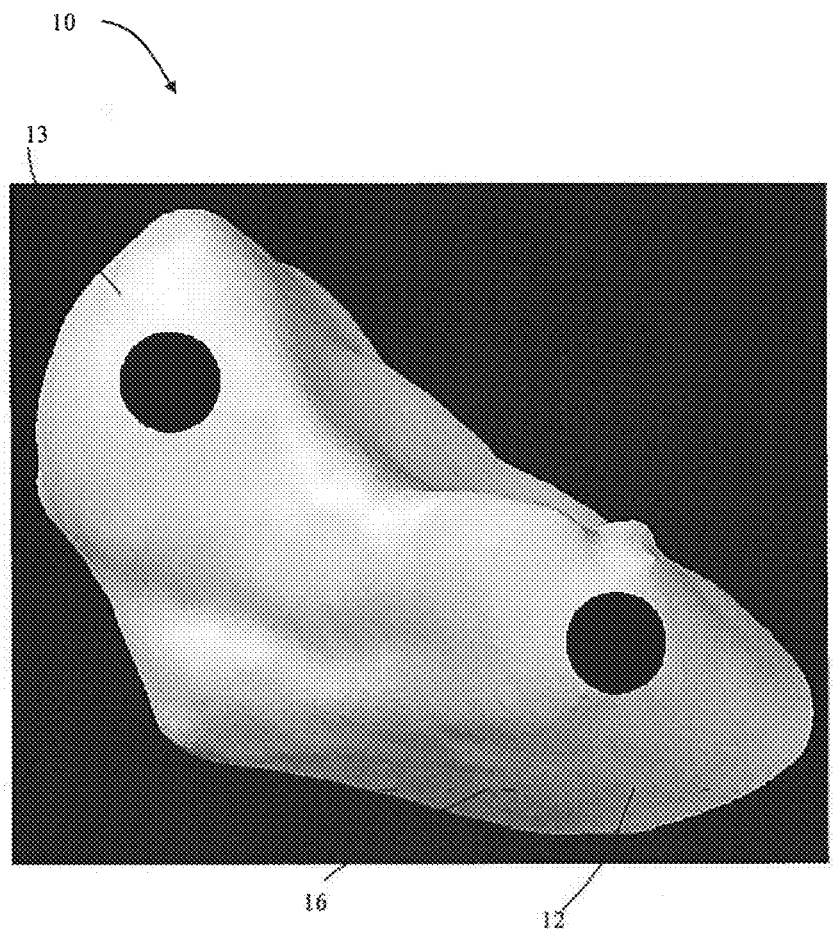

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

The present invention is described with respect to replacing a scaphoid bone of a wrist of a human patient. However, the invention can apply equally to other bones in other mammalian patients. For example, the invention can apply to any other bone in a mammalian wrist, hand, ankle or foot. Therefore, the description below should not be taken to restrict the scope of the invention to the replacement of scaphoid bones only.

In accordance with one embodiment of the present invention, there is provided an orthopaedic implant 10 (hereinafter referred to as "implant") for replacing a scaphoid bone of a patient. As best seen in FIGS. 3A to 3F, the implant 10 is one-piece and replicates in overall size and shape the scaphoid bone being replaced based on characterization of the patient's contralateral scaphoid bone. By virtue of the inventors' surprising discovery that the left and right scaphoid bones of a human patient are substantially identical mirror images of each other, the size and shape of the implant based on the patient's other scaphoid bone is an anatomical replica or imitation of the scaphoid bone being replaced.

The implant 10, as with a scaphoid bone of a human, comprises a body 12 having a number of articulating surfaces, specifically a capitate articulating surface 14, a trapezium articulating surface 15, a radius articulating surface 16 and a lunate articulating surface 17. By articulating surface it is meant a surface having at least one contact surface portion on which an articulating piece such as a bone may articulate such as by rubbing, sliding or rolling.

Unlike the scaphoid bone which the implant 10 is replacing, the implant 10 has at least one attachment element which can be in the form of an opening or a hole formed on or through its body. In a preferred embodiment, the attachment element is two openings 18, 20 formed through the implant body 12 for securing the implant 10 to ligaments, tendons or other soft tissue of the wrist or hand of the patient by sutures or other means. The openings 18, 20 are positioned so that they do not substantially compromise the physical properties of the implant 10, such as its strength. Preferably, the openings are positioning distally and proximally to one another. Instead of openings, the implant 10 can be provided with other means of securing the implant to soft tissue such as protrusions (not shown) or other openings formed on its surface (not shown). Preferably, the implant 10 is a single piece but can also be made of a number of pieces, made of the same or different materials for example, which are formed or joined together.

The implant 10 can be made of any suitable biocompatible material such as biocompatible metals, polymers, ceramics and composites. The implant 10 can be porous or coated. By "suitable biocompatible material" is meant a biocompatible material which has adequate physical properties to withstand the biomechanical forces applied to it once it is implanted into the patient and adequate wear properties for its intended use. Preferably, the implant 10 is made of a metal such as a titanium alloy, a cobalt chromium alloy or a vitallium alloy, according to known biocompatible metal alloy compositions.

In an embodiment where the implant is not a single piece (not shown), the pieces of the implant may be made of different materials. For example, the body and the attachment element can be made of different materials. If the attachment element is an opening or openings, the opening(s) can be partially or fully lined or covered by a bioactive material to encourage bone or soft tissue growth for enhanced attachment. Similarly, if the attachment element is a protrusion, the parts of the protrusion intended for attachment to the adjacent tissue can be formed of, or covered by, a material suitable for enhancing or encouraging soft or hard tissue growth.

Figure 4:
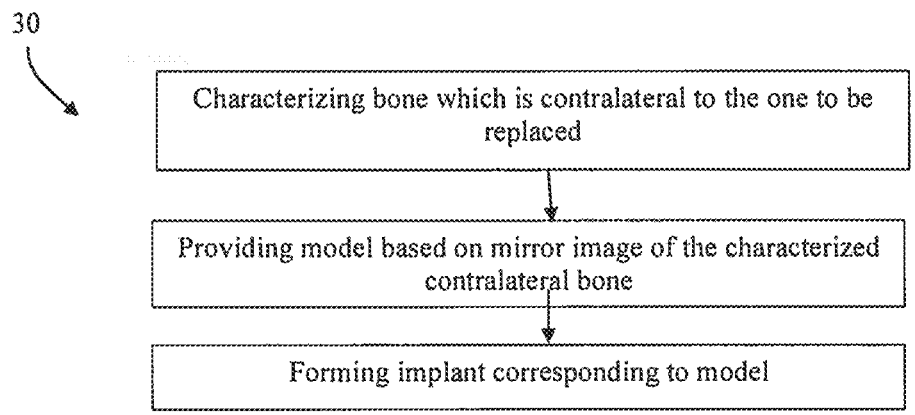
FIG. 4 illustrates a method of making the implant of FIGS. 3A to 3F according to an embodiment of the present invention.

A method 30 of making the implant 10 is summarized in FIG. 4 and includes characterizing the bone which is contralateral to the one to be replaced, providing a model based on a mirror image of the characterized contralateral bone. Preferably, the bone being replaced by the implant 10 is characterized by imaging or any other non-invasive method. In this embodiment, the bone being replaced by the implant 10 is the scaphoid bone. By imaging it is meant characterizing the overall size and shape of the bone which may include methods other than imaging. Of course, in cases where the scaphoid bone to be replaced is sufficiently intact, the implant can be based on the scaphoid bone to be replaced. The implant could also be used to replace a portion of the scaphoid bone rather than the entire scaphoid bone. In this way, a customized implant for the patient can be made. This means that the implant will imitate or replicate the anatomical shape and size of the bone being replaced.

In a preferred embodiment, the patient's scaphoid bone which is contralateral to the scaphoid bone being replaced by the implant is characterized using imaging techniques such as Magnetic Resonance Imaging (MRI), Computed Tomography (CT), positron emission tomographic (PET) or ultrasound scanning and appropriate software, such as 3D Doctor™ or AutoCAD™, to produce three-dimensional (3D) images of the contralateral bone which can be processed and converted to a 3D solid implant. Preferably, MRI is used to capture tomographic image or measurement data of the bone and three-dimensional image data of the bone is produced based on this data. Alternatively two-dimensional images of the contralateral bone can be captured and converted to three-dimensional images by other means. In another alternative, the corresponding contralateral bone can be characterized using techniques other than imaging which are then converted to three-dimensional images before making the implant. What is important is that the outer dimensions and shape of the bone to be replaced are characterized to a reasonable degree of accuracy before being modeled. The surface topography need not be characterized to such an extent. Identifying and imaging the larger surface features may suffice.

The actual or mirror 3D images of the corresponding contralateral bone can be processed before making a model or implant based on them. The processing can include modifying the surface features or topography to accentuate or smooth the surface features, for example to reduce facets to approximate a smooth surface on the implant. The processing can also include forming the attachment elements, such as the openings through the body of the imaged bone. The processing is preferably performed digitally but can also be carried out in other known ways. Alternatively, the attachment elements, such as the openings 18, 20, can be formed on the implant 10 itself after the three-dimensional model of the implant is made from the images, such as by drilling or other known techniques.

A preferred method of forming the implant 10 from the images is using stereolithography using Cobalt Chrome printing. Alternatively, any other method of making the implant 10 from the imaged or otherwise characterized bone can be used, such as moulding or related techniques. The implant can be made pre-operatively or intra-operatively.

Advantageously, by virtue of the inventors' discovery that the scaphoid bones of the left and right hands of humans are substantially identical mirror images of one another, the undamaged scaphoid bone of a patient can be used to model a scaphoid implant to replace the damaged scaphoid bone. By using imaging techniques such as MRI, CT or any other non-invasive imaging technique, trauma to the patient is minimized. In this way, an implant which is anatomically substantially identical or similar to the scaphoid bone which it is replacing can be produced. Implantation of such a customized implant in the patient ensures that the biomechanics of the patient's wrist and hand movement is optimized and wear and trauma to the wrist and hand is minimized.

Figure 5A:
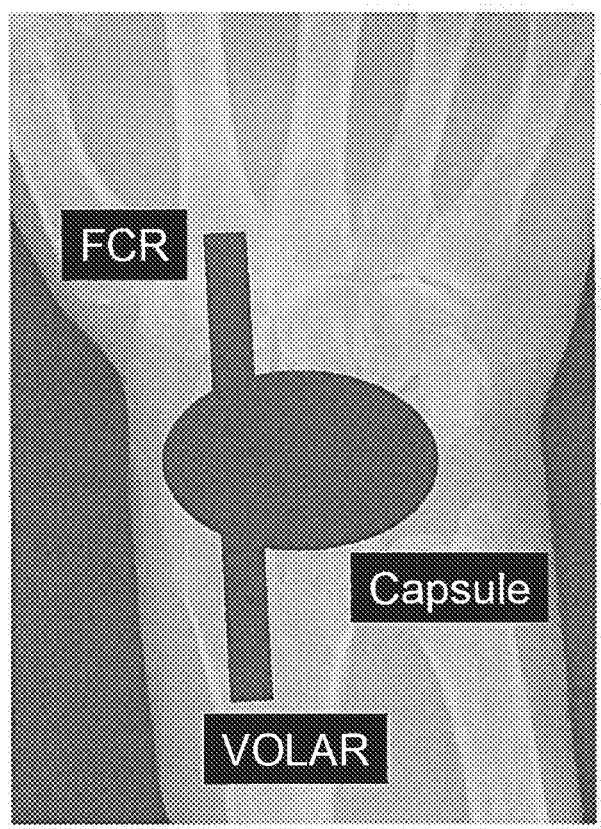
FIGS. 5A, 5B and 5C are x-rays of a human wrist with indications of location of the volar FCR tendon and capsule, the dorsal DIC and SL ligaments, and the ends of the dorsal DIC and SL ligaments which are attachable to the implant of FIGS. 3A to 3F.
Figures 5B, 5C:
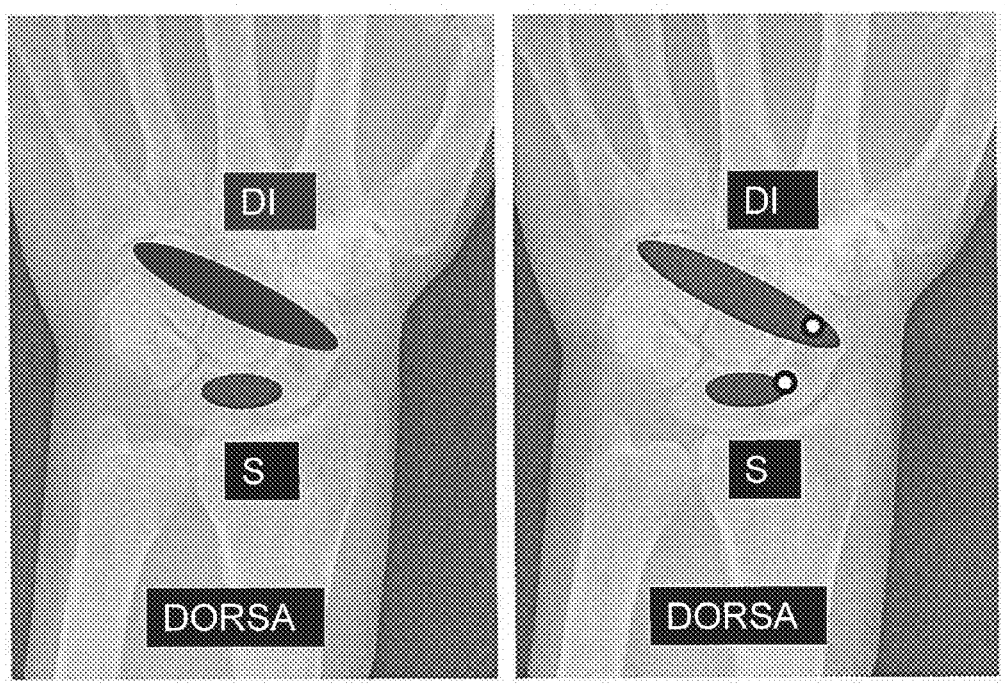
Figure 6:
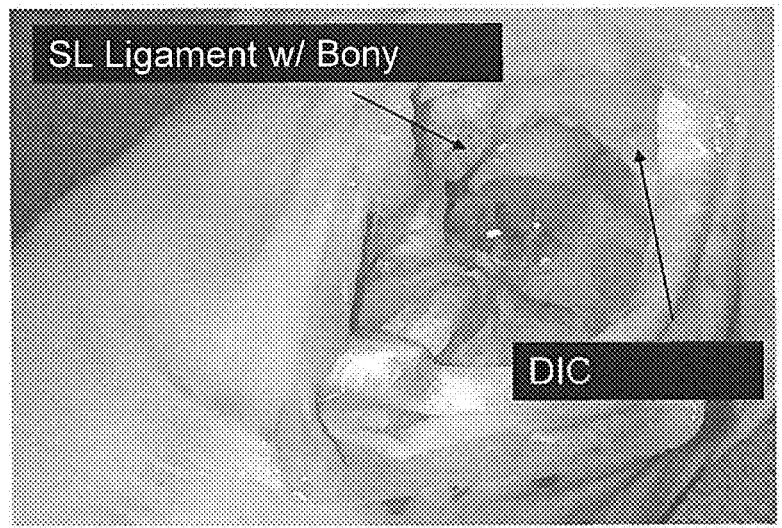
FIG. 6 illustrates the implant of FIGS. 3A to 3F in use.

In use, the implant 10 replaces the scaphoid bone when the scaphoid bone is damaged, such as by disease or fracture. The scaphoid bone and/or the scaphoid bone fragments are first removed from the patient before being replaced with the implant 10. The implant 10 is secured in position by attaching it to some of the soft tissue structures in the wrist by means of the attachment element, such as the openings 18, 20 of the implant 10. The inventors have identified that attachment of the holes 18, 20 of the implant 10 to the SL ligament, the DIC ligament, the capsule and the FCR provides a balanced and stable positioning of the implant 10 to avoid dislocation, provide biologic ingrowth and provide an anatomic replacement of the scaphoid bone. Also, as the scaphoid is not fixed to the radius, flexibility of movement of the wrist is obtained. The positions of these soft tissue structures are identified in FIG. 5B, FIG. 5B and FIG. 5C. FIG. 6 shows the implant in position.

A surgical procedure for implantation of the scaphoid implant involves either a Dorsal or a Volar (Henry's) incision. Firstly, the scaphoid bone being replaced is exposed taking care to protect the SL ligament proximally. The DIC is then exposed and protected distally. The scaphoid bone to be replaced is cut at the waist and the DIC is sharply dissected from the scaphoid bone distally. The scaphoid bone is then excised leaving intact the four soft tissue structures: the dorsal SL ligament with its bony block, the dorsal DIC ligament, the volar capsule and the volar FCR with its bony block. The scaphoid implant is then placed into position and a Bunnel suture in the DIC ligament is passed through the distal hole of the implant and then sutured to the FCR tendon. A Bunnel suture in the SL ligament is passed through the proximal hole of the implant and then sutured to the volar capsule. The stability of the implant 10, once in place, is checked by flexing the patient's wrist. The surgical and post-operative techniques then continue in conventional manner.

Figure 7A:
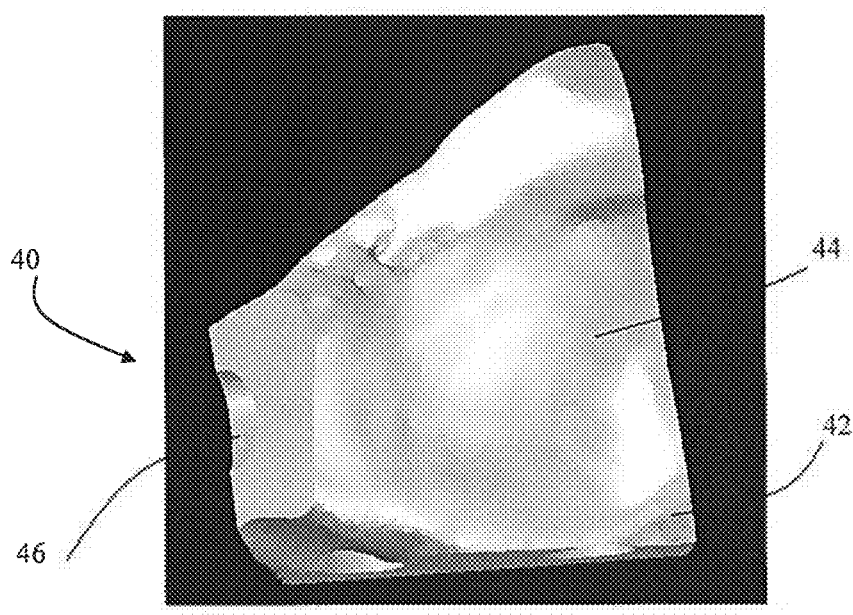
FIGS. 7A and 7B illustrate an orthopaedic implant according to another embodiment of the present invention when viewed from (A) an articulating surface, and (B) a non-articulating surface.
Figure 7B:
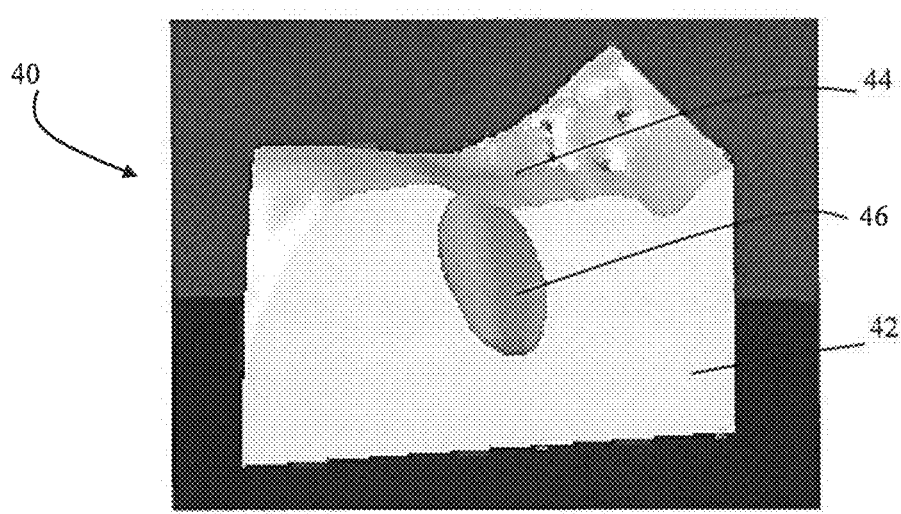

From another aspect, there is provided an orthopaedic implant 40 (hereinafter referred to as "radius component 40") (FIGS. 7A and 7B) for resurfacing or replacing a portion of the distal end of the radius bone and for providing an articulating surface against which the scaphoid implant 10 can articulate. Accordingly, the radius component 40 comprises a body 42 attachable to the radius at the distal end of the radius and an articulating surface 44. At least a portion of the articulating surface 44 is shaped and sized to articulate against at least a portion of the radius articulating surface 16 of the scaphoid implant 10. The body 42 of the radius component 40 has an attachment element, preferably in the form of openings (holes) 46 formed therethrough for screws, nails or other fixation devices, to fix the radius component 40 to the radius bone. Preferably, the radius component 40 replaces only the portion of the radius surface which would articulate against the scaphoid implant. In this way, preservation of the radius bone mass can be maximized.

The articulating surface 44 of the radius component 40 corresponds substantially in topography or surface features to the radius articulating surface 16 of the scaphoid implant 10. This helps to minimize wear and subsequent trauma due to articulation of the scaphoid implant 10 against the radius component 40.

The radius component 40 can be made of any suitable biocompatible material such as biocompatible metals, polymers, ceramics and composites. Preferably, the radius component 40 is made of ultra-high molecular weight polyethylene (UHMWPE) which has suitable wear properties. Alternatively, just the articulating surface 44 of the radius component 40 can be made of UHMWPE or other suitable biomaterial.

In an alternative embodiment, the radius component 40 may be adapted to replace any other surface which articulates against the scaphoid implant 10.

Figure 8:
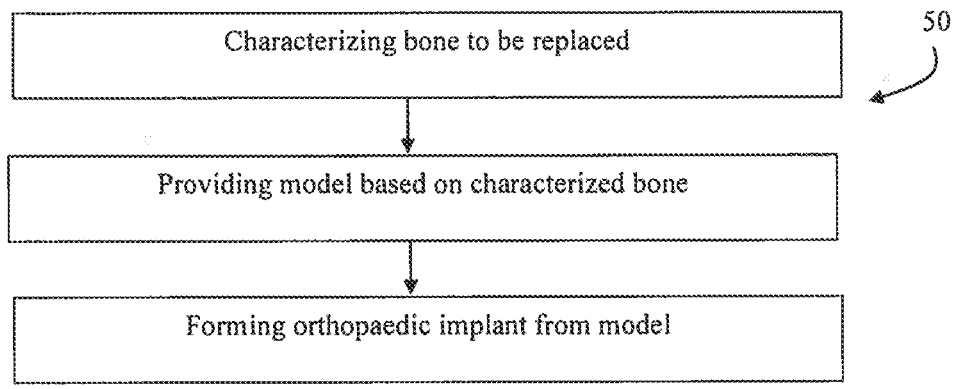
FIG. 8 illustrates a method of making the orthopaedic implant of FIGS. 7A and 7B according to an embodiment of the present invention.

A method 50 of making the radius component 40 is summarized in FIG. 8. Briefly, the method 50 includes forming a model of the radius component 40 before making the radius component 40 itself. The outer dimensions of the model of the radius component are based on the outer dimensions of a corresponding portion of the patient's radius (actual or contralateral). The dimensions and macro-topography of the 3D model of the articulating surface 44 of the radius component 40 are based on the radius articulating surface 16 of the scaphoid implant 10.

Figure 9:
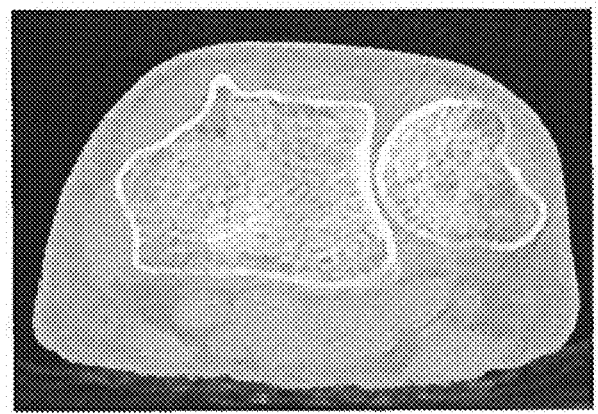
FIG. 9 illustrates an MRI of a patient's radius to be partially replaced by the orthopaedic implant of FIGS. 7A and 7B according to the method of FIG. 8.
Figure 10:
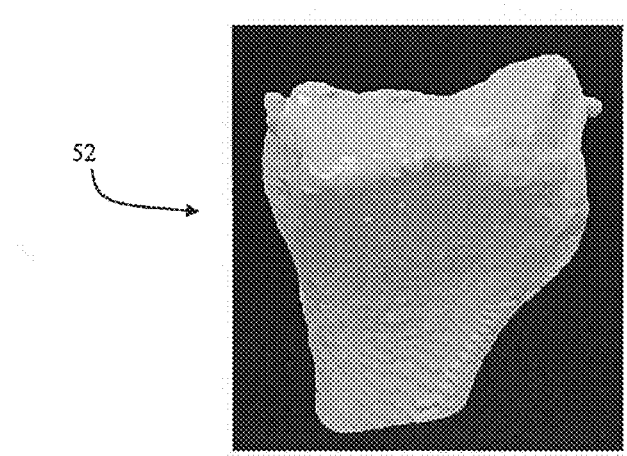
FIG. 10 illustrates a model of the patient's radius based on the MRI of FIG. 9.

The modelling of the outer dimensions of the radius component 40 is achieved by imaging the radius component which is to be resurfaced (FIG. 9) to preferably obtain a 3D imaged model 52 of the distal radius (FIG. 10) in the same way as described above for the scaphoid bone. If the radius component to be resurfaced has an abnormal morphology or is also diseased or damaged, the patient's contralateral radius component may be imaged. The features of the radius articulating surface 16 of the scaphoid implant 10 are then applied to the 3D imaged model 52 of the distal radius. In this way, imaging of the radius component can be avoided which may be inconvenient or problematic due to cartilage of the radius surface not being visible by CT. Alternatively, the articulating surface of the radius component 40 may be based on an image of the radius articulating surface of the radius itself rather than the implant. It will be appreciated that the either the scaphoid implant 10 or the radius component 40 may be formed first with a surface topography based on the actual scaphoid bone or the radius bone being replaced, or their contralateral counterparts. What is important is that the surface topography of the articulating surfaces of the scaphoid implant 10 and the radius component 40 correspond such that they can matingly engage with one another in order to minimize wear between these surfaces.

Figure 11A:
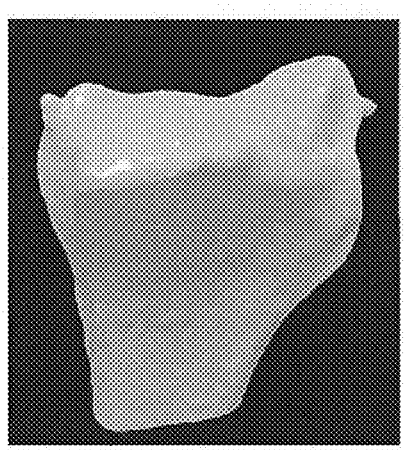
FIGS. 11A and 11B illustrate processed images of the model of FIG. 10.
Figure 11B:
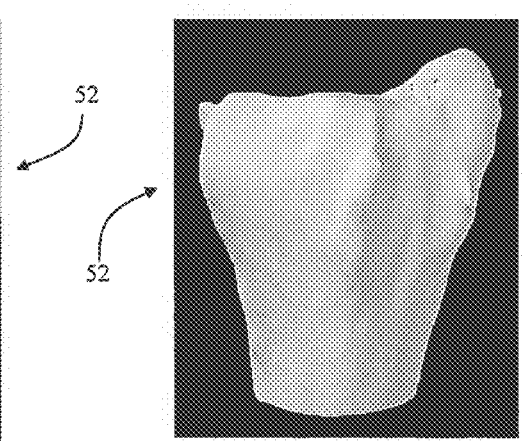
Figure 12A:
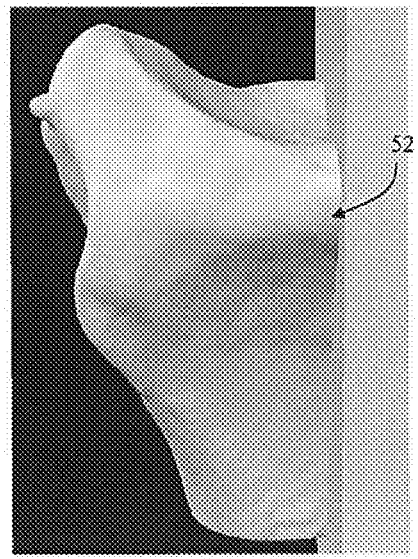
FIGS. 12A to 12I illustrate further processing of the model of FIG. 10 to arrive at the final model of the orthopaedic implant of FIGS. 7A and 7B.
Figure 12B:
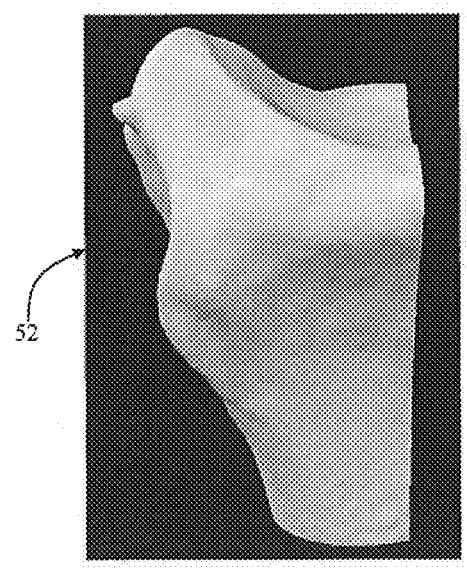
Figure 12C:
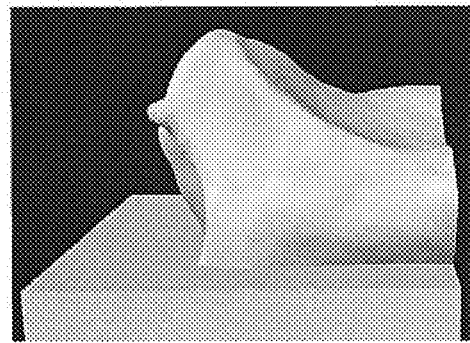
Figure 12D:
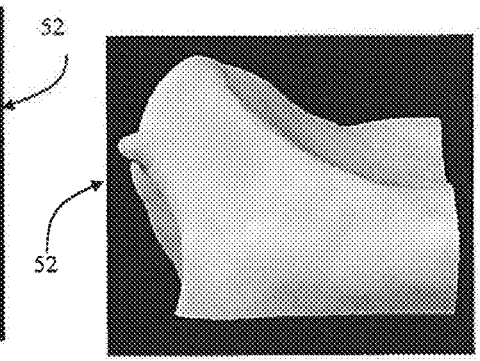
Figure 12E:
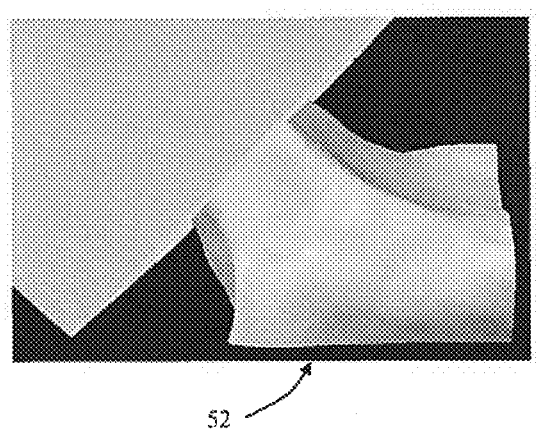
Figure 12F:
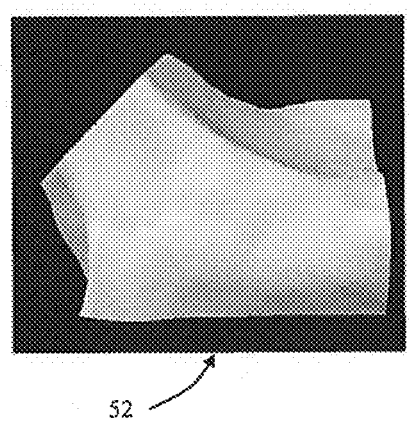
Figure 12G:
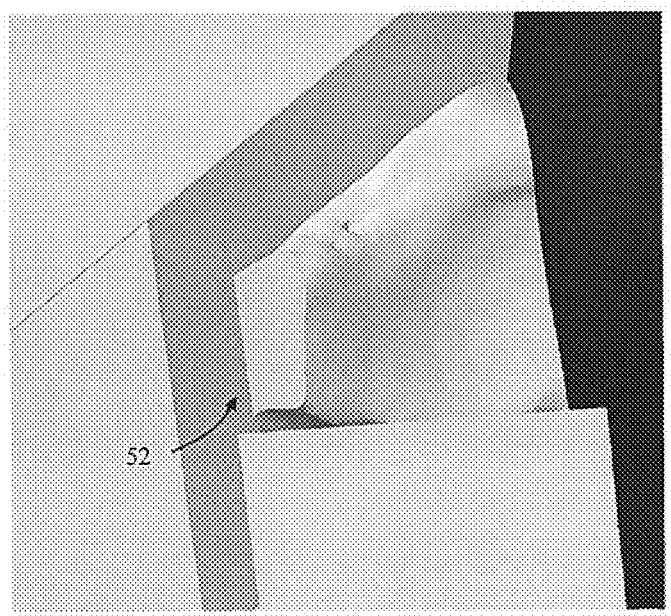
Figure 12H:
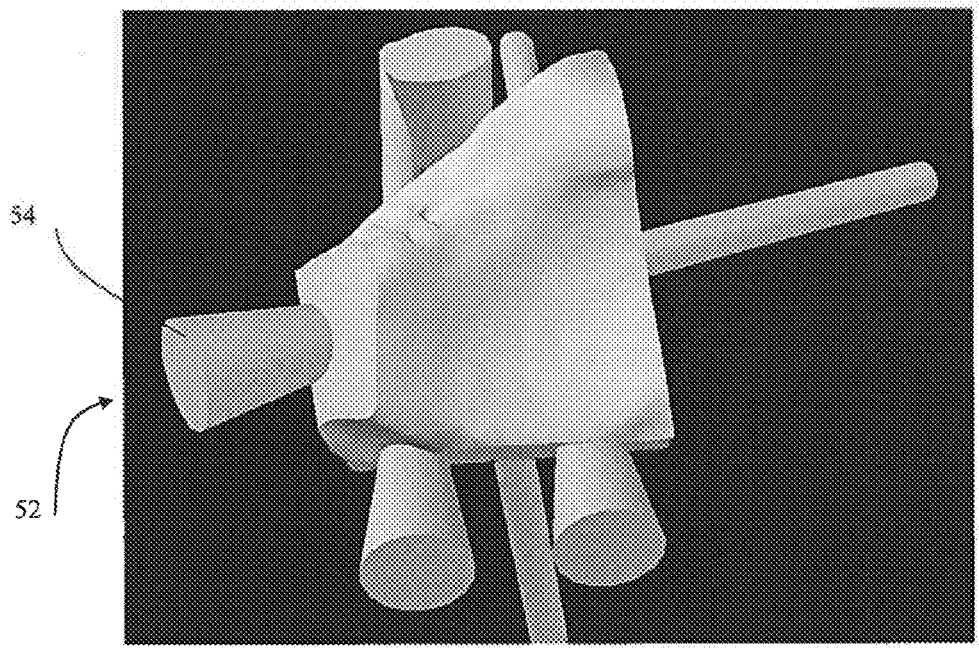
Figure 12I:
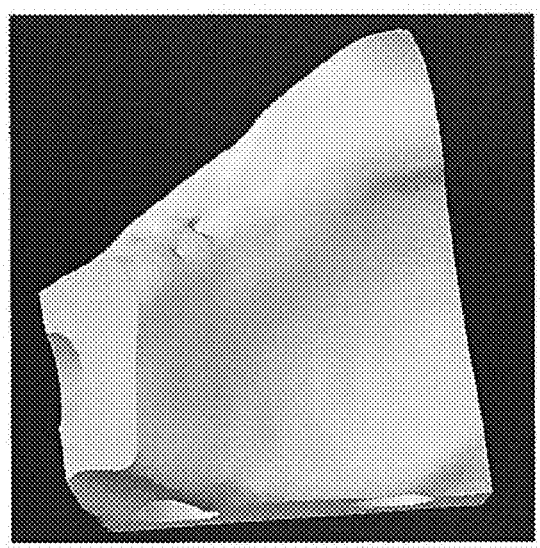
Figure 13A:
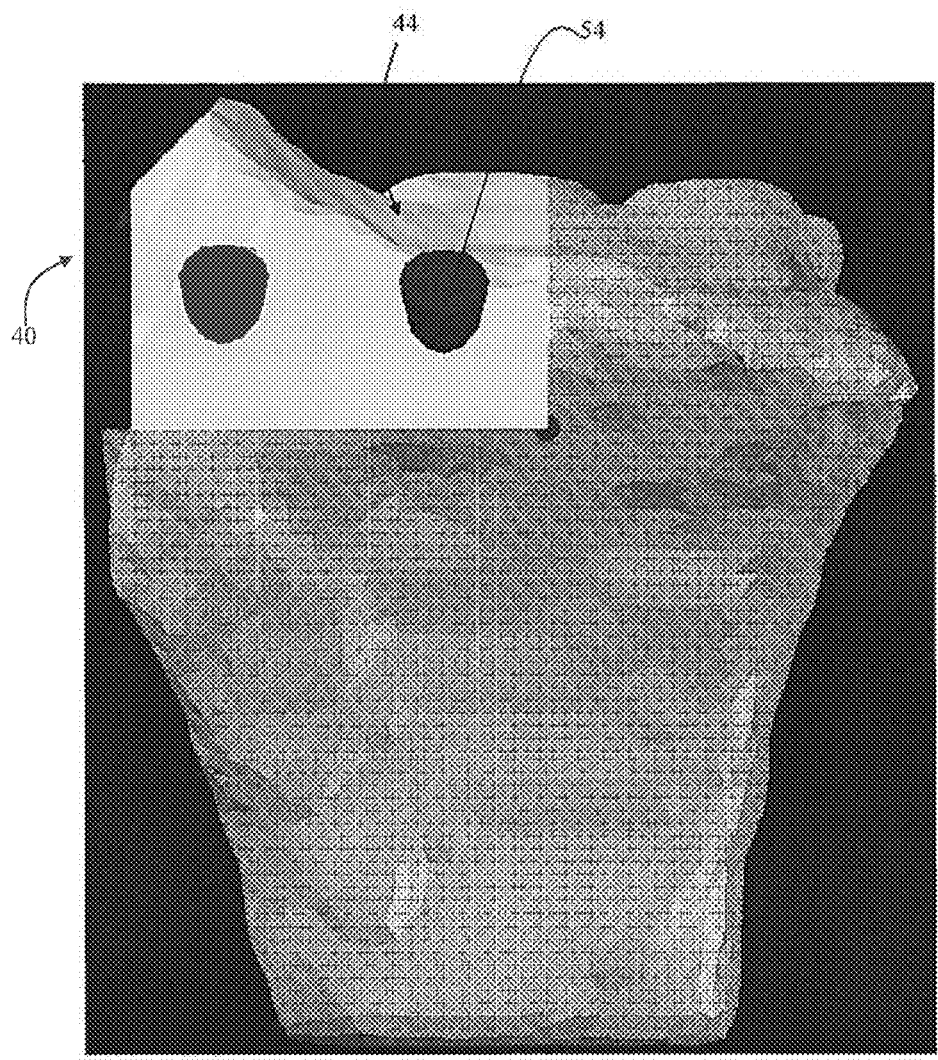
FIGS. 13A to 13D illustrate (A) an anterior, (B) a lateral, (C) a posterior and (D) a perspective view of the orthopaedic implant of FIGS. 7A and 7B in use.
Figure 13B:
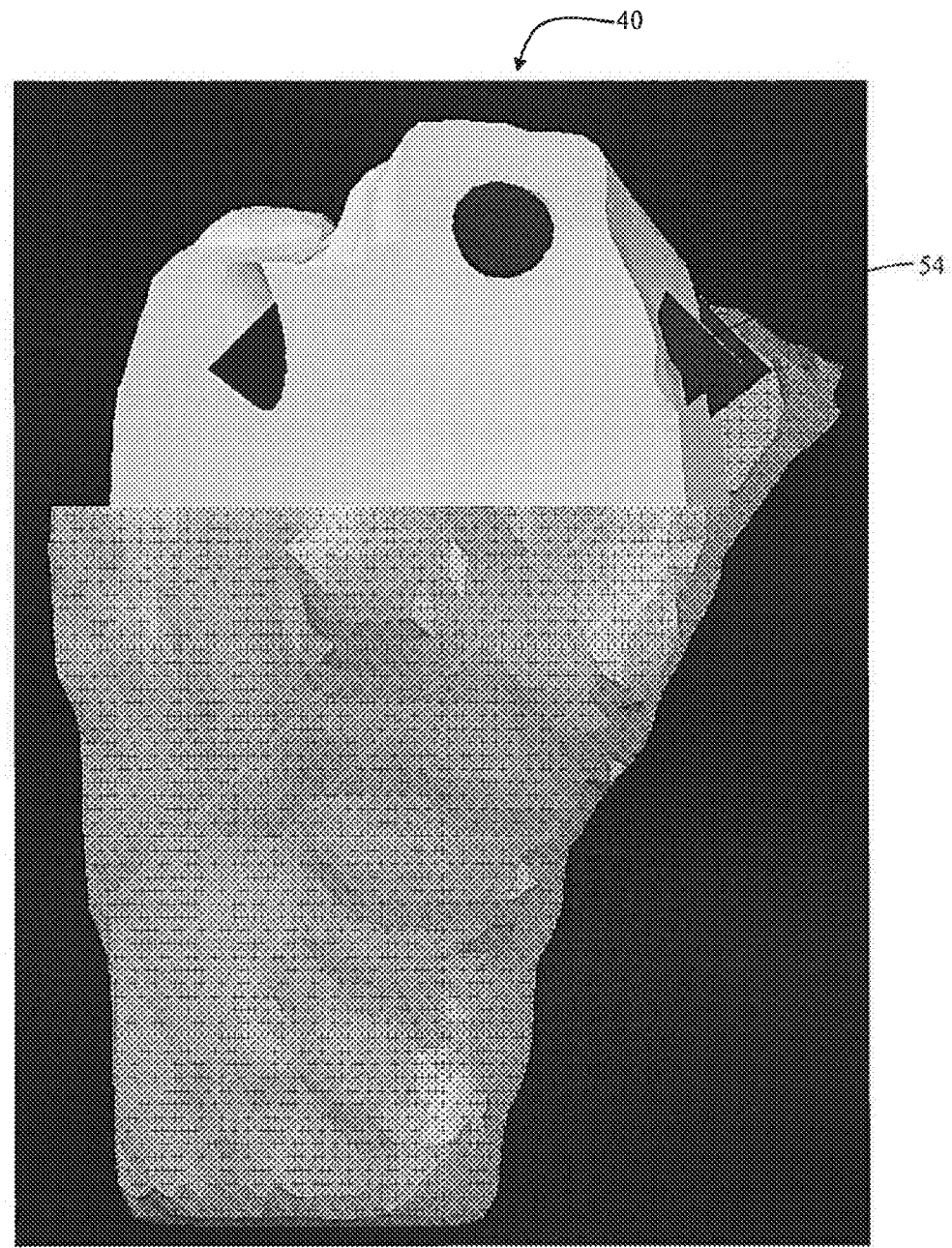
Figure 13C:
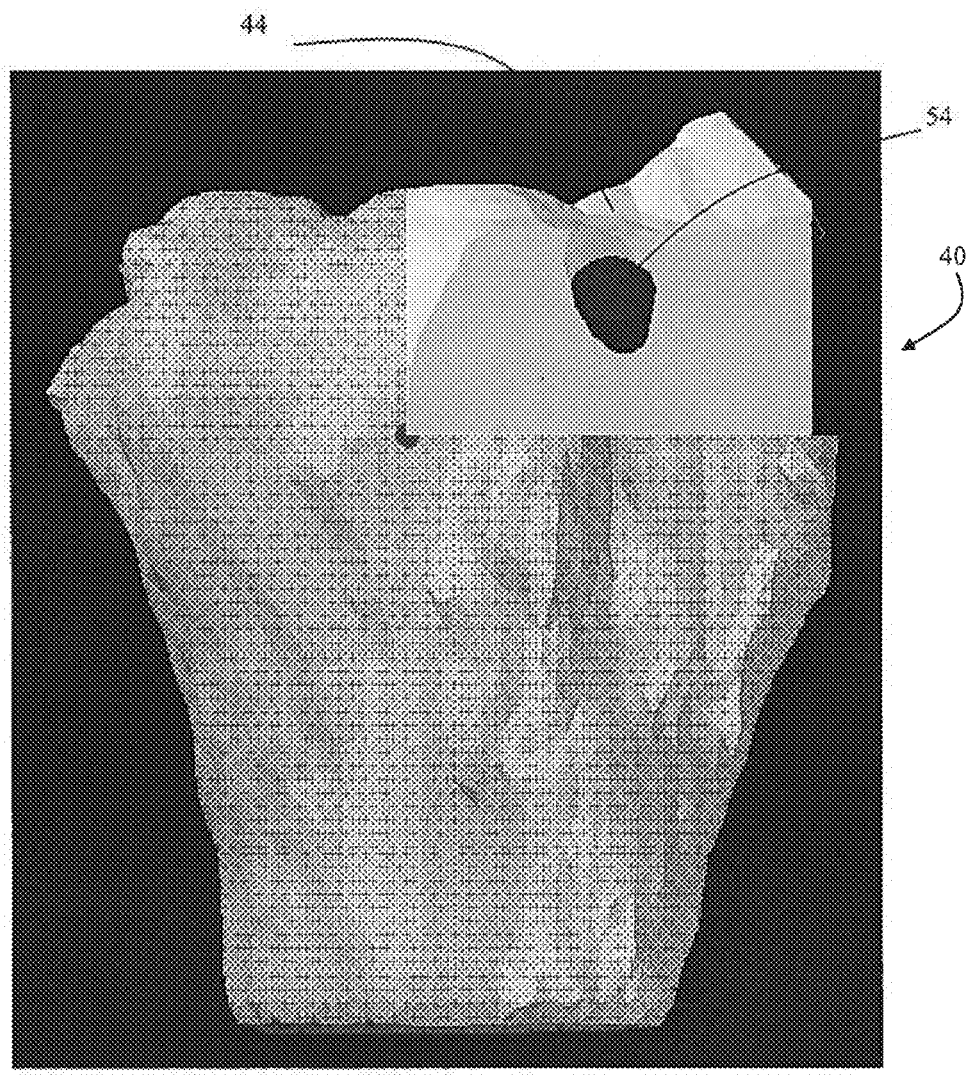
Figure 13D:
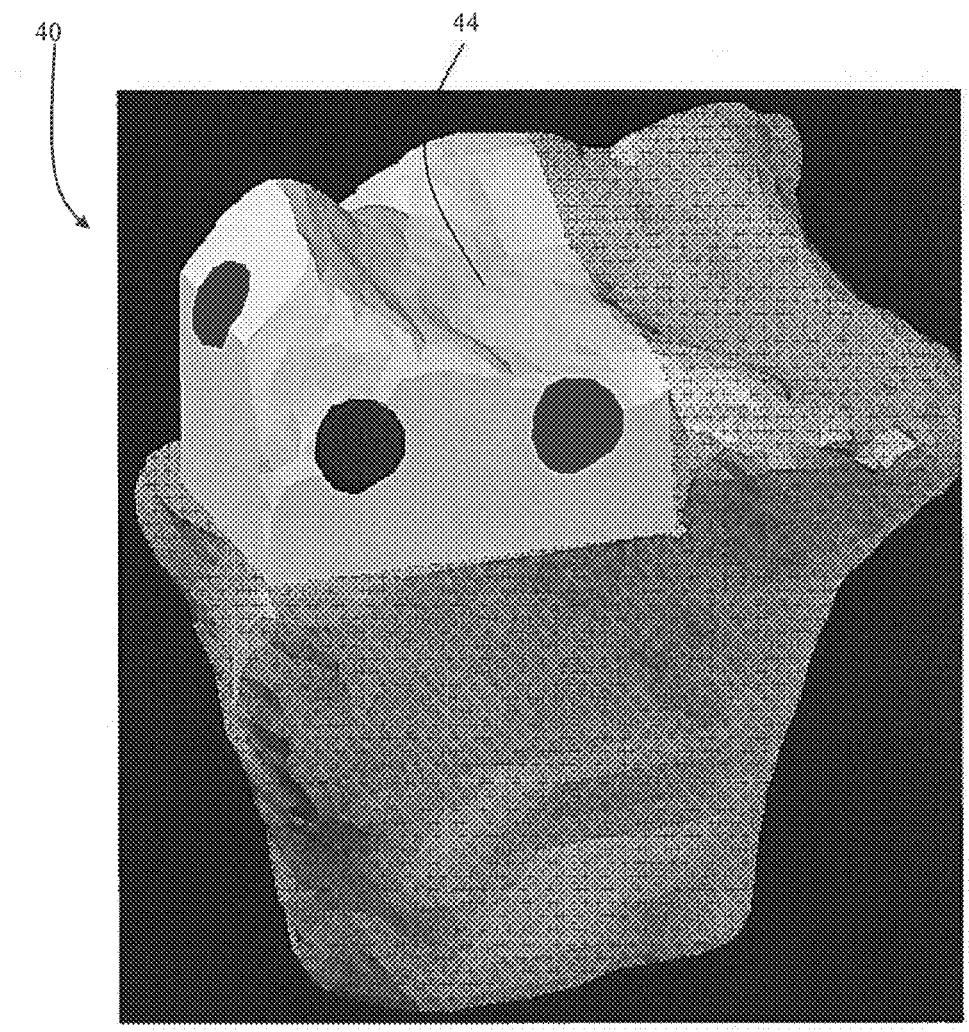
Figure 14:
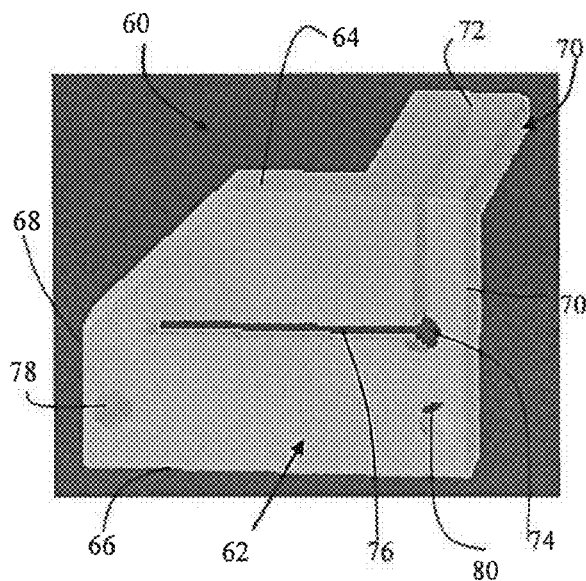
FIG. 14 illustrates a perspective view of a first device according to an embodiment of the present invention for preparing a bone for implantation of the orthopaedic implant of FIGS. 7A and 7B.
Figure 15:
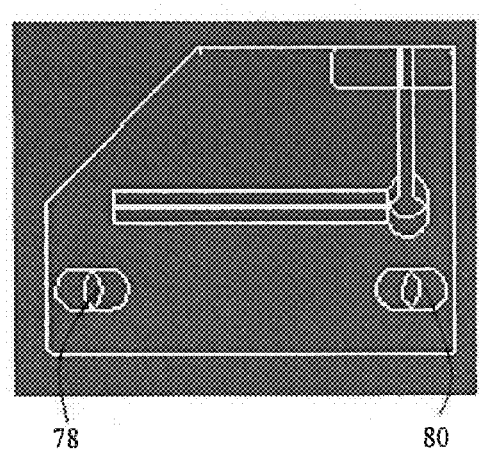
FIG. 15 illustrates a plan view of a plate portion of the first device of FIG. 14.
Figure 16:
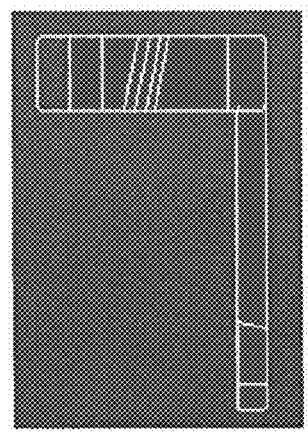
FIG. 16 illustrates a first end view of the first device of FIG. 14.
Figure 17:
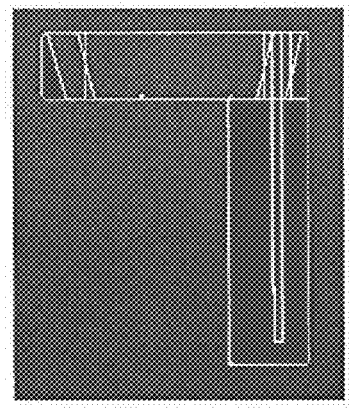
FIG. 17 illustrates a second end view of the first device of FIG. 14.

The 3D imaged model including surface features of the distal radius can then be processed, if necessary, to smooth and/or reduce facets (FIGS. 11A and 11B). The processing can include trimming the model 52 of the outer dimensions of the radius component 40 until it is the required size and shape (FIGS. 12A to 12G). Preferably, the imaged model 52 is trimmed to retain only the terminal distal radius without the styloid. The processing can also include the addition of attachment elements, such as openings, for receiving fixation elements 54, such as screws or nails, to the imaged model 52 for fixing the radius component to the radius (FIG. 12H) in order to determine the positioning of the openings or screw holes. The resultant imaged model 56 is illustrated in FIG. 12I. The radius component is then formed from the final imaged model 56 using conventional methods such as stereolithography or molding. Alternatively, the attachment elements may be formed on the radius component 40 after the radius component 40 is formed rather than first modeled on the 3D model 52.

Advantageously, the articulating surfaces of the scaphoid implant 10 and the radius component 40 will match which will minimize wear between them. This will also avoid misalignment which may affect the other bones of the wrist and lead to bone disease, such as arthritis, or other damage.

In use, the radius component 40 is implanted into the distal portion of the radius bone (FIGS. 13A to 13D). The articulating surface 44 of the radius component 40 is flush with the intact adjacent distal surface of the radius. Fixation elements 54 such as screws and nails hold the radius component 40 in place.

The distal portion of the radius must be prepared prior to implantation of the radius component 40 by excising material from the area in which the radius component 40 is to be implanted.

Accordingly, according to another aspect of the invention there is provided a guiding device 60 or jig for assisting in the preparation, e.g. the cutting, of the distal portion of the radius prior to implantation of the radius component 40 (FIGS. 14 to 17). The guiding device 60 comprises a truncated orthogonal-shaped plate 62 which is shaped and sized to be positioned adjacent the distal end of the radius bone. The plate 62 has an upper edge 64, a lower edge 66, a scaphoid side edge 68 and a lunate side edge 70. One corner of the upper edge 64 is truncated (between the scaphoid side edge 68 and the upper edge 64). From the other corner of the upper edge 64 (at the lunate side edge) extends an arm 70 with a free end at substantially right angles to the plate 62. There is a first slot 72 extending along the arm 70 and having an arm end which stops short of the free end of the arm 70. The first slot 72 also extends in the other direction, from the arm 70 to substantially halfway across the plate 62, between the plate upper and lower edges 64, 66. There is a substantially circular opening 74 at this plate end of the first slot 72. There is a second slot 76 extending from the circular opening towards the scaphoid side edge 68 and parallel to the upper and lower edges 64, 66. The first and second slots 72, 76 define cutting guides. There are two openings 78, 80 along the lower edge 66 of the plate 62 one at or near each of the lower edge corners, for receiving fixing means such as wire, screws or nails.

Figure 18A:
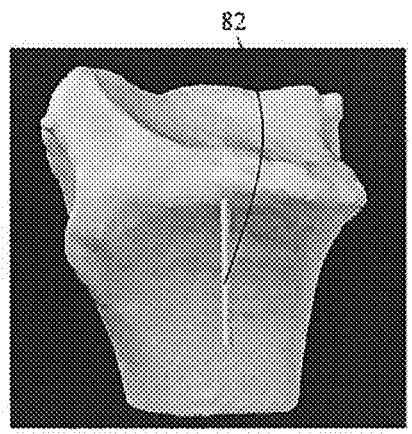
FIGS. 18A to 18F illustrate use of the first device of FIG. 14 to implant the orthopaedic implant of FIGS. 7A and 7B.
Figure 18B:
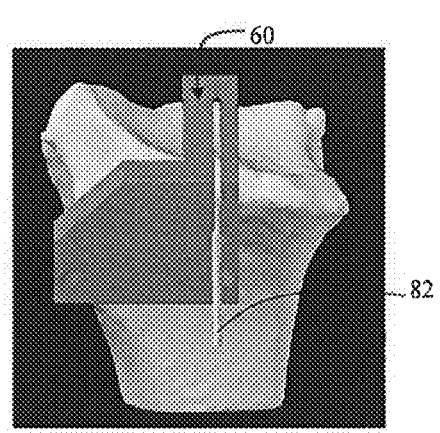
Figure 18C:
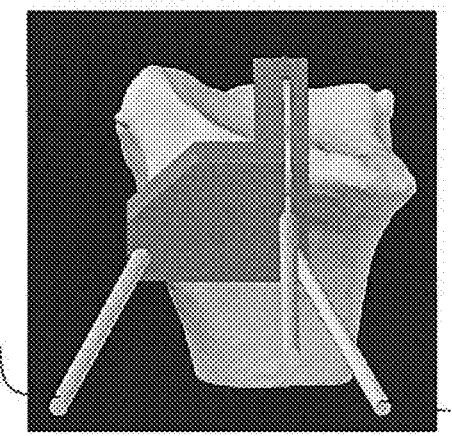
Figure 18D:
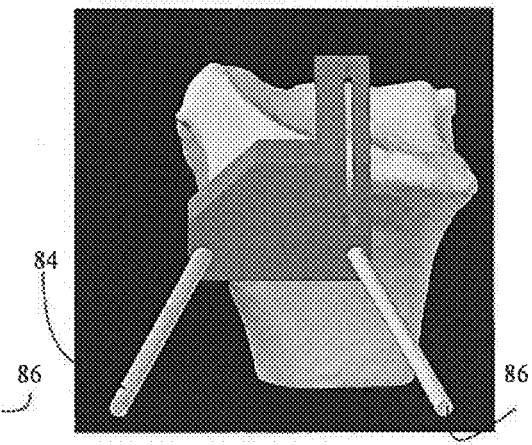
Figure 18E:
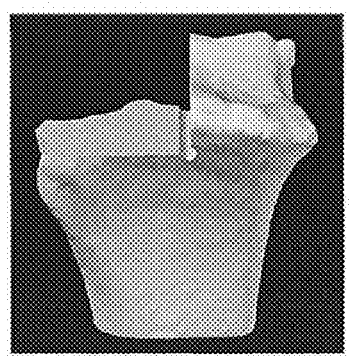

In use, the guiding device 60 is positioned over the distal end of the bone such that the arm 70 abuts the radius surface at the distal end of the bone and the plate 62 abuts the adjacent radius surface. A first k-wire 82, preferably 0.7 mm diameter, or other fixation device, is inserted through the radius bone parallel to the ridge between the scaphoid and lunate fossas leaving a free end protruding from the radius bone (FIG. 18A). The guiding device 60 is positioned adjacent the distal end of the radius with the guiding device arm 70 being placed over the radius distal end between the scaphoid fossa and the lunate fossa. The circular opening 74 at the plate end of the first slot 72 receives the free end of the first k-wire 82 (FIG. 18B). The guiding device 60 is further secured in this position using a second and a third k-wire 84, 86, preferably each having a 1 mm diameter, or other fixation devices, one at each opening 78, 80 at the lower edge corners of the plate (FIG. 18C). The first k-wire is removed (FIG. 18D) before cutting the radius along the first and second slots 72, 76, preferably using a reciprocating device such as a micro-oscillating saw, to excise the scaphoid fossa (FIG. 18E). The distal radius is now ready for implantation of the radius component 40.

Figure 18F:
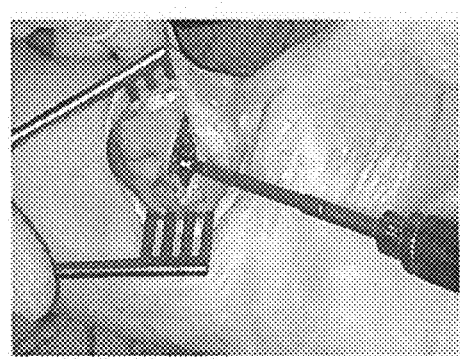
Figures 19, 20:
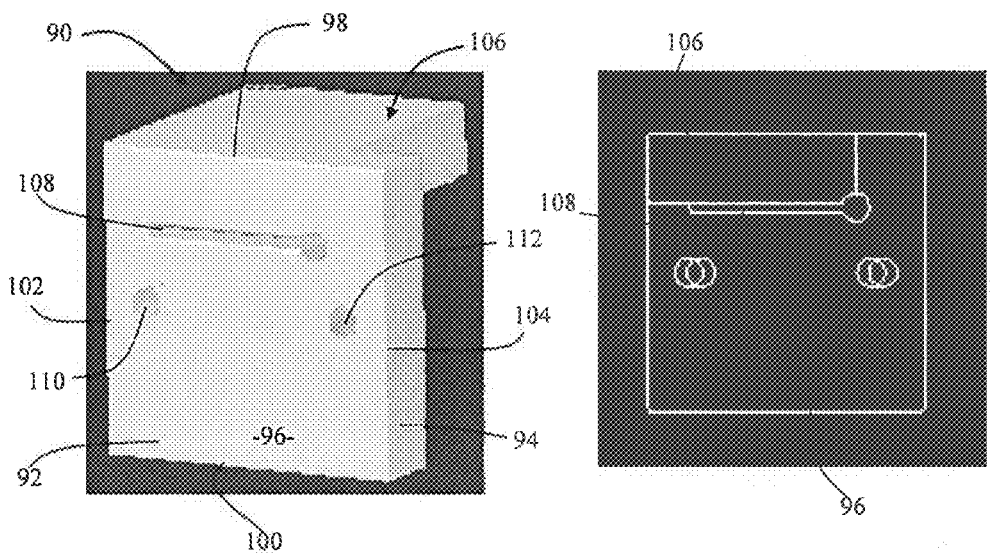
FIG. 19 illustrates a perspective view of a second device according to an embodiment of the present invention for preparing a bone for implantation of the orthopaedic implant of FIGS. 7A and 7B.
FIG. 20 illustrates a plan view of a plate portion of the second device of FIG. 19.
Figure 21:
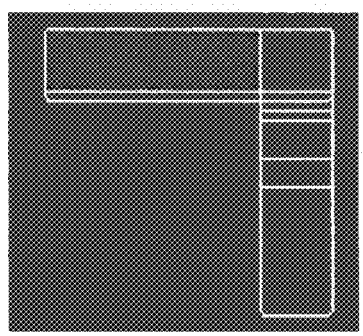
FIG. 21 illustrates a first end view of the second device of FIG. 19.
Figure 22:
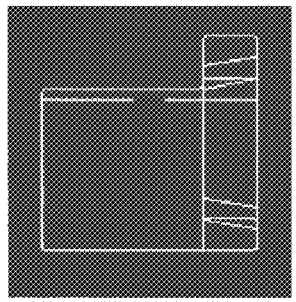
FIG. 22 illustrates a second end view of the second device of FIG. 19.

The radius component 40 can be positioned on and fixed to the prepared distal radius in the following way. The radius component 40 is placed into position on the excised position of the radius with the scaphoid articulating surface 44 facing outwardly. A screw, nail 54 or other fixing device, preferably a 2.4 cortical screw, is inserted percutaneously, radially. Three further screws, preferably locking screws, are then inserted: 2 volar and 1 dorsal. The radial cortical screw is then replaced with a further locking screw (FIG. 18F).

In practice, the excision or preparation of the distal radius may be performed before the scaphoid bone is replaced by the scaphoid implant 10 to take advantage of the space provided by the excision of the radius bone.

FIGS. 19 to 22 illustrate a further guiding device 90 which is for guiding the controlled removal of additional bone, if required, from the distal radius. This further guiding device 90 will be referred to as a trimming guide device. The trimming guide device 90 comprises an orthogonal plate 92 having an inner face 94, an outer face 96, an upper edge 98, a lower edge 100, and two oppositely facing side edges 102, 104. An arm 106 extends from the upper edge 98 at substantially right angles from the plate inner and outer faces 94, 96 so the plate 92 and the arm 106 form an 'L' shape. A slot 108 extends across the plate 92 between its two side edges 102, 104 near its upper edge 98. The ends of the slot 108 end short of the side edges 102, 104. Two openings 110, 112 are provided in the plate 92, one near each side edge and closer to the lower edge than the slot. The slot 108 defines a cutting guide.

In use, the trimming guide device 90 is positioned adjacent the cut portion of the distal radius with the arm 106 overlying the cut radius portion. The trimming guide device 90 is arranged so that the height of the slot 108 is aligned with the required cut to the bone. The device 90 is held in this desired position by placing k-wires or other fixation devices (not shown) through the plate openings 110, 112. The k-wires are at the points in the jig in order to ensure that the trimming guide device 90 does not weaken the radius by notching. The radius bone is cut along the slot 108 by inserting a cutting edge of a cutting device, such as a micro-oscillating saw, in the slot 108 which is then guided by the slot 108.

Figure 23:
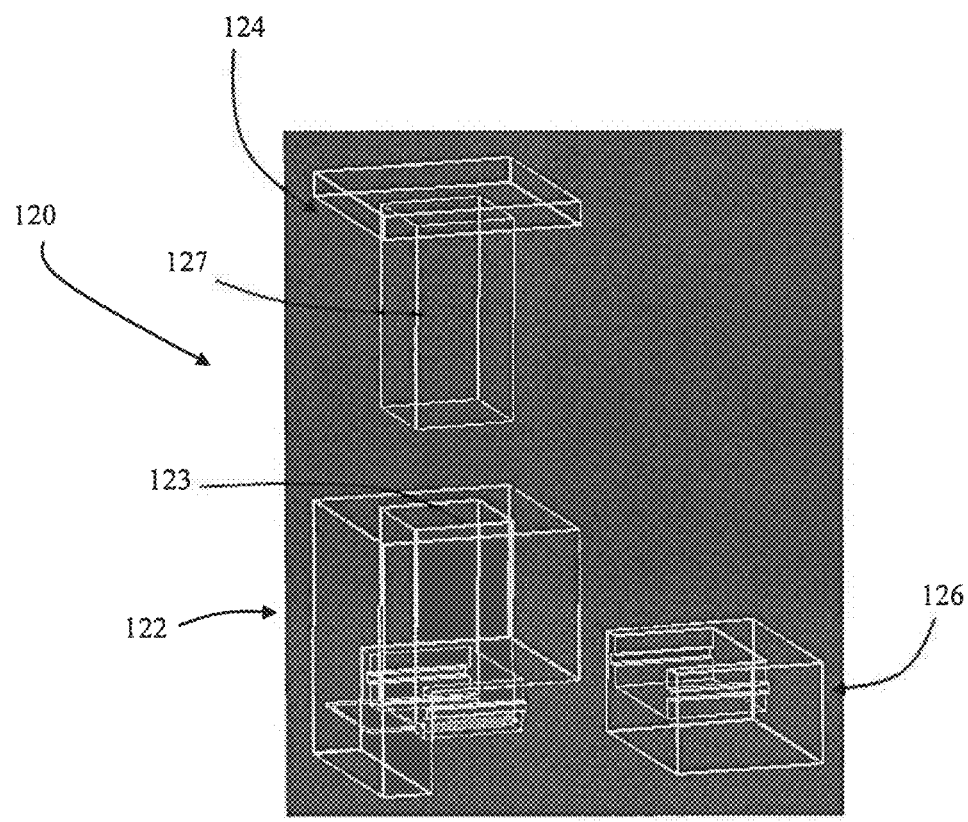
FIG. 23 is a perspective view of a third device according to an embodiment of the present invention for preparing a bone for implantation of the orthopaedic device of FIGS. 7A and 7B.
Figure 24:
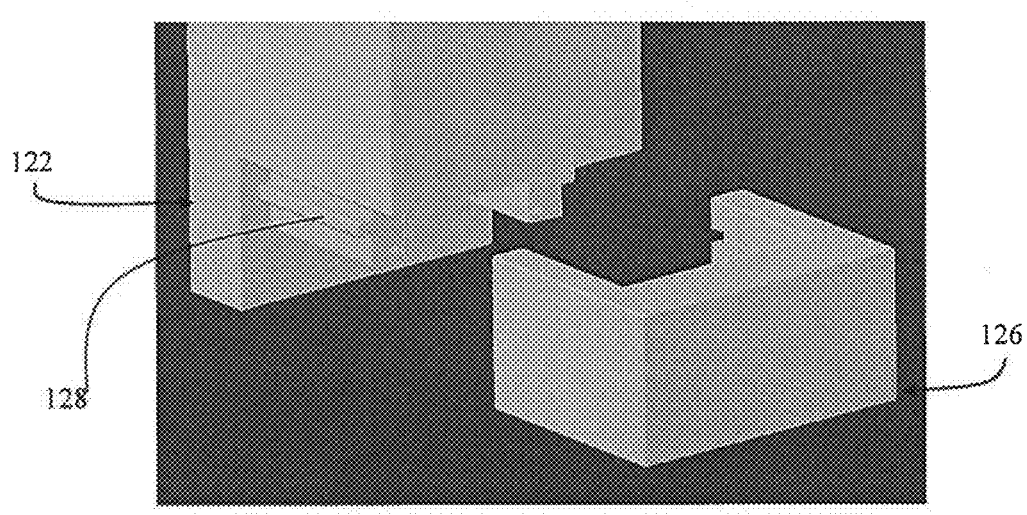
FIG. 24 is a close-up view of a portion of one side of the device of FIG. 23.
Figure 25:
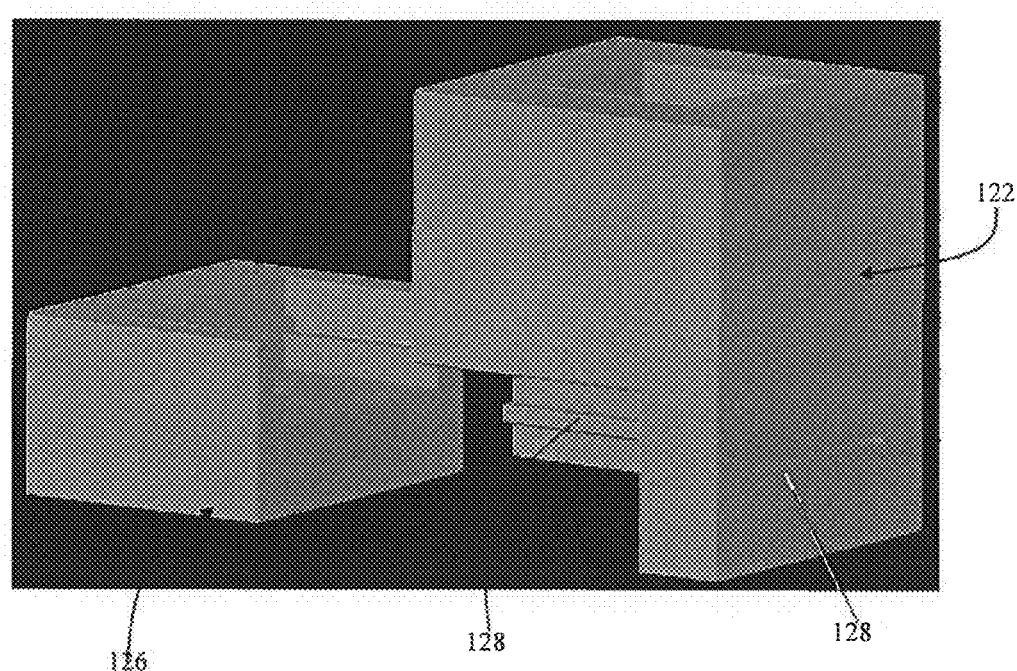
FIG. 25 is a close-up view of a portion of another side of the device of FIG. 23.

FIG. 23 illustrates a correcting device 120 for correcting the excision of too much bone from the distal radius, for example in the case of surgeon error. The correcting device allows for the cutting of a sliver of bone from the excised bone which can then be grafted onto the radius distal end. The correcting device 120 comprises three components: a tubular portion 122 having a bore 123 running through, an end portion 124 for closing one open end of the bore 123, and a plunger portion 126 having a plunger 127 which can be received in the other open end of the bore 123. The end portion 124 and the corresponding open end of the bore 123 are illustrated in FIGS. 24 and 25. It can be seen that the end portion 124 slides over runners 128 in the tubular portion 122 to engage with the tubular portion 122 to close the open end of the bore 123. In use, the end portion 124 is engaged with the tubular portion 122 to close the open bore end. The excised bone piece removed from the distal radius is inserted into the bore 123 of the tubular portion 122, flat side down, from the other open end. The plunger 127 is placed into the open end of the bore 123 and pressed downwardly to engage with the bone piece and hold the bone piece in place to enable slivers of bone to be cut from the bone piece. Once cut, the bone sliver is retrieved by removing the end portion from the tubular portion 122. Accordingly, a slot 128 is provided through a wall of the tubular portion corresponding to the position of the bone sliver when in position in the tubular portion (FIG. 25). The slot can receive a blade or a cutting edge of a cutting device. The cutting device can be any device suitable for cutting bone such as a reciprocating device e.g. an oscillating saw. The correcting device 120 is provided with different sizes/depths to enable the cutting of different thicknesses of bone slivers from the excised bone piece. The bone slivers will then be placed back onto the cut surface of the distal radius.

The guiding device 60, trimming guide device 90 and the correcting device 120 can be made from any suitable material in conventional manner. Preferably, they are made from metal. They may be provided in kit form either individually or altogether.

It should be appreciated that the invention is not limited to the particular embodiments described and illustrated but includes all modifications and variations falling within the scope of the invention as defined in the appended claims. For example, instead of screws, nails, k-wires or other wires used for securing, other fixation devices can equally be used. The aspects of the present invention can be applied to bones other than the scaphoid bone as will be clear to a person skilled in the art, e.g. the talus, calcaneus, navicular, and cuneiforms bones as well as all small bones of the hand and foot.

EXAMPLES

The following examples are illustrative of the applicability of the present invention and are not intended to limit its scope. Modifications and variations can be made therein without departing from the spirit and scope of the invention. Although any method and material similar or equivalent to those described herein can be used in the practice for testing of the present invention, the preferred methods and materials are described.

Example 1

The scaphoid implant 10 of the present invention was made and implanted in the manner as described above into the wrist of a cadaver, including use of the cutting guide jigs. FIGS. 26A and 26B, 27A and 27B, and 28A and 28B show x-rays taken of the cadaver's wrist after implantation and during maximum flexion and extension.

Example 2

Figure 29A:
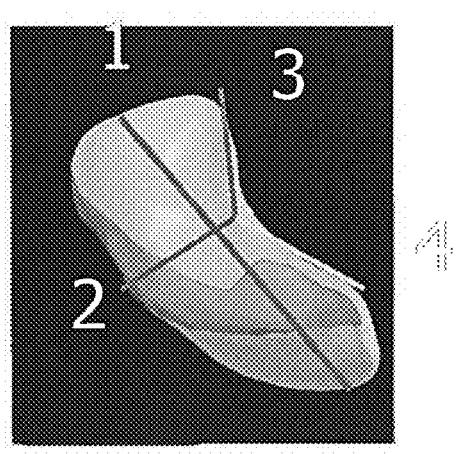
FIG. 29 illustrates the geometry of a scaphoid bone and its mirror image with its contralateral scaphoid bone according to Example 2.
Figure 29B:
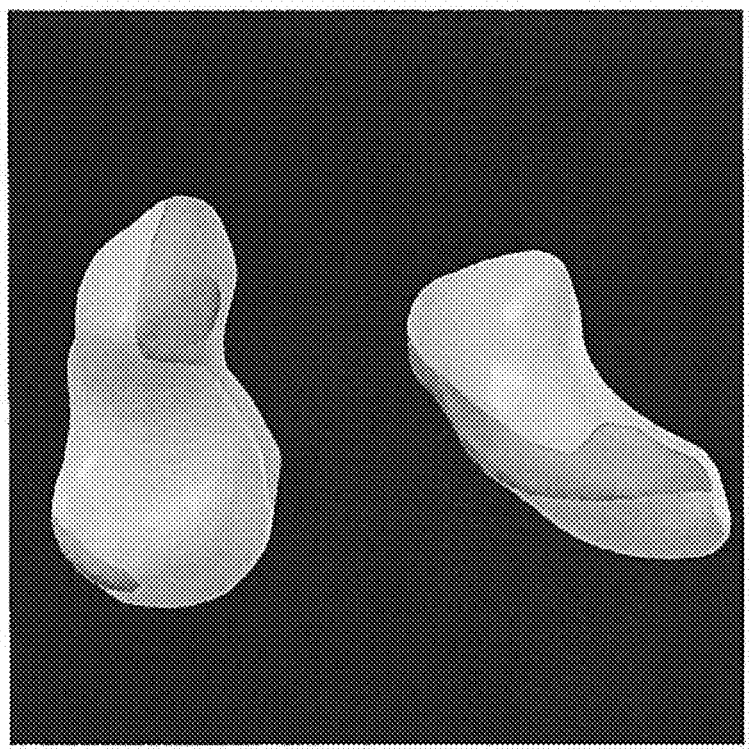

The inventors performed a cadaveric study using MRI and CT on the symmetry of contralateral scaphoid bones. Surprisingly, they found that the contralateral scaphoid bones are mirror images of one another, as determined by four geometrical features: 1) long axis, 2) waist length, 3) distal pole and 4) proximal pole (FIG. 29A).

A CT and MR investigation of 12 pairs of cadaveric wrists was made in neutral position. After imaging, each wrist was dissected and the bones were cleaned of any connective tissue. The bones were measured along their longest axis and the volume of each bone was determined by water displacement measurements.

Lunate Measurements
Antero-dorsal diameter (16.96 mm±1.6)
Medio-lateral diameter (12.8 mm±1.37)
Height/max length
Volume
Surface Area.
Scaphoid Measurements
Height/Max length
Volume
Surface Area.

A statistical analysis was carried using the Pearson correlation coefficient comparing CT/MRI and anatomical measurements of the right and left bones.

The invention claimed is:

1. A method for making a scaphoid implant for replacing the entirety of a first scaphoid bone in a wrist of a patient, the method comprising:
    characterizing at least a portion of a second scaphoid bone by obtaining data representative of the size and/or shape of the portion of the second bone, the second scaphoid bone being on the contralateral side of the patient from the first scaphoid bone;
    providing a three-dimensional digital model of the scaphoid implant based on a mirror image of the second scaphoid bone; and
    forming the scaphoid implant based on the three-dimensional digital model for replacing the first scaphoid bone.

2. A method according to claim 1, wherein the characterizing of the second bone comprises imaging the portion of the second bone using Magnetic Resonance Imaging or Computed Tomography.

3. A method according to claim 1, further comprising characterizing a surface topography of an articulating bone intended to articulate with a surface of the first bone, and applying the characterized surface topography to the three-dimensional digital model or to the implant.

4. A method according to claim 1, further comprising adding an attachment element to the three-dimensional digital model or to the implant, the attachment element being at least one opening in the implant for receiving a fixing element to attach the implant to surrounding soft or hard tissue in use.

5. A method according to claim 1, wherein the implant is formed from the three-dimensional digital model by stereolithography.

6. A method according to claim 1, further comprising the step of processing the three-dimensional digital model of the implant, including modifying a surface feature by applying a surface topography, wherein the surface topography to be applied is based on an articulating surface topography of an adjacent bone intended to articulate with a surface of the first bone, and characterizing the articulating surface topography of the adjacent bone and applying the characterized surface topography to the three-dimensional digital model.

7. A method for making an orthopaedic scaphoid implant to replace all of a first scaphoid bone, the method comprising:
    characterizing at least a portion of a second scaphoid bone by obtaining data representative of the size and/or shape of the portion of the second bone, the second scaphoid bone corresponding to said first scaphoid bone and being on the contralateral side of the patient;
    providing a model of the orthopaedic scaphoid implant based on a mirror image of the second scaphoid bone located on the contralateral side of the patient, the model being a three-dimensional digital image;
    processing the model, including modifying a surface feature by applying a surface topography, wherein the surface topography to be applied is based on an articulating surface topography of an articulating bone intended to articulate with a surface of the first scaphoid bone to be replaced, and characterizing the articulating surface topography of the adjacent bone and applying the characterized surface topography to the model; and
    forming the orthopaedic scaphoid implant based on the model.

8. A method according to claim 7, wherein the characterizing comprises imaging the at least a portion of the second bone corresponding to the first bone to be replaced.

9. A method according to claim 7, wherein the surface feature modifying includes adding an attachment element to the model, and forming the attachment element on the orthopaedic implant.

10. A method according to claim 9, wherein the attachment element is at least one opening in the orthopaedic implant for attaching the orthopaedic implant to surrounding soft or hard tissue in use.

11. A method according to claim 7, wherein the orthopaedic implant is formed from the model by stereolithography.

12. A method according to claim 7, further comprising making a replacement articulating component for articulating against a portion of the orthopaedic implant in use, the method comprising:
    providing a model of an articulating bone to be replaced; and
    forming the replacement articulating component from the model.

13. A method according to claim 12, wherein providing the model of the articulating bone includes imaging the articulating bone or the patient's contralateral articulating bone.

14. A method according to claim 12, further comprising processing the model before forming the replacement articulating component, the processing including modifying a surface to apply a surface topography.

15. A method according to claim 14, wherein the processing includes characterizing a surface topography of the articulating bone or the patient's contralateral articulating bone and applying it to the model.

16. A method according to claim 14, wherein the processing includes adjusting the outer dimensions of the model to minimize the amount of bone being replaced.

* * * * *